US006720167B1

(12) United States Patent
Federici et al.

(10) Patent No.: US 6,720,167 B1
(45) Date of Patent: Apr. 13, 2004

(54) INSECTICIDAL BACTERIA, AND METHODS FOR MAKING AND USING THEM

(75) Inventors: Brian A. Federici, Riverside, CA (US); Dennis K. Bideshi, Perris, CA (US); Hyun-Woo Park, Riverside, CA (US); Margaret C. Wirth, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 52 days.

(21) Appl. No.: 09/639,576

(22) Filed: Aug. 14, 2000

(51) Int. Cl.[7] .................... C12P 21/02; C12N 15/75; C12N 1/20; C07H 21/04
(52) U.S. Cl. ............... 435/69.1; 435/320.1; 435/252.3; 435/71.3; 435/471; 435/252.31; 435/252.5; 536/24.1; 536/23.7
(58) Field of Search .................... 536/24.1, 23.7; 435/320.1, 252.3, 71.3, 471, 252.5, 252.31, 69.1

(56) References Cited

U.S. PATENT DOCUMENTS 6,140,104 A    10/2000   Lereclus et al.  ............ 435/243

OTHER PUBLICATIONS

Sedlak et al. Regulation by overlapping promoters of the rate of synthesis and deposition into crystalline inclusions of *Bacillus thuringiensis* delta–endotoxins. J. Bacteriol. 182:734 (2000).*

Nicolas et al. Respective role of the 42– and 51–kDa components of the *Bacillus sphaericus* toxin overexpressed in *Bacillus thuringiensis*. FEMS Microbiol. Lett. 106:275 (1993).*

Federici, "Genetic Engineering of Endotoxin Synthesis In *Bacillus thuringiensis* for Improved Efficacy", abstracts of presentations on selected topics at the XIVTH International Plant Protection Congress (IPPC) Jul. 25–30, 1999, International Convention Center, Jerusalem, Israel.

Agaisse, H. et al., "STAB–SD: a Shine–Dalgarno sequence in the 5' untranslated region is a determinant of mRNA stability," *Molecular Microbiology* 20(30), 633–643 (1996).

Agaisse, H. et al, "How Does *Bacillus thuringiensis* Produce So Much Insecticidal Crystal Protein,?" *Journal of bacteriology*, 177(1):6027–6032 (Nov. 1995).

Bar, E. et al., "Cloning and Expression of *Bacillus thuringiensis israelensis* δ–Endotoxin DNA in *B. sphaericus*," *Journal of Invertebrate Pathology*, 57:149–158 (1991).

Baum, J. et al. "Regulation of insecticidal crystal protein production in *Bacillus thuringiensis*," *Molecular Microbiology*, 18(1):1–12,(1995).

Baumann, L. et al., "Sequence Analysis of the Mosquitocidal Toxin Genes Encoding 51.4– and 41.9–Kilodalton Proteins from *Bacillus sphaericus* 2362 and 2297," *Journal of Bacteriology* 170 (5)045–2050 (May 1988).

Bourgouin, C. et al., "Transfer of the Toxin Protein Genes of *Bacillus sphaericus* into *Bacillus thuringiensis* subsp. *israelensis* and Their Expression,*Applied and Environmental Microbiology*," 56(2)340–344 (Feb. 1990).

Crickmore, N. et al., "Revision of the Nomenclature for the *Bacillus thuringiensis* Pesticidal Crystal Proteins," *Microbiology and Molecular Biology Reviews*, 62(3):807–813 (Sep. 1998).

Lereclus, D. et al., "Overproduction of Encapsulated Insecticidal Crystal Proteins in a *Bacillus thuringiensis* spoOA Mutant," *Bio/Technolgoy* 13:67–71 (Jan. 1995).

Li, T. et al., Coexpression of cyt/Aa of *Bacillus thuringiensis* subsp, *israelensis* with *Bacillus sphaericus* Binary Toxin Gene in Acrystalliferous Strain of *B. thuringiensis, Current Microbiology*, 40:322–326 (2000).

Park, H. et al, "Differential enhancement of Cry2A versus Cry11A yields in *Bacillus thuringiensis* by use of the cry3A STAB mRNA sequence," *FEMS Microbiology Letters*, 181:319–327 (1999).

Park, H. et al, "Optimization of Cry3A Yields in *Bacillus thuringiensis* by Use of Sporulation–Dependent Promoters in Combination with the STAB–SD mRNA Sequence," *Applied and Environmental Microbiology*, 64(10):3932–3938 (Oct. 1998).

Poncet, S. et al., "Improvement of *Bacillus sphaericus* Toxicity against Dipteran Larvae by Integration via Homologous Recombination, of the Cry11A toxin Gene from *Bacillus thuringiensis* subsp. *israelensis*," *Applied and Environmental Microbiology*, 63(11):4413–4420 (Nov. 1997).

Poncet, S. et al., "Transfer and expression of the cry/VB and cry/VD genes of *Bacillus thuringiensis* subsp. *israelensis* in *Bacillus sphaericus* 2297," *FEMS Microbiology Letters*, 117:91–96 (1994).

(List continued on next page.)

Primary Examiner—James Ketter
Assistant Examiner—Daniel M. Sullivan
(74) Attorney, Agent, or Firm—Townsend Townsend and Crew LLP

(57) ABSTRACT

The invention relates to the discovery that nucleic acid sequences comprising a BtI or BtII promoter, or a combination of a BtI and a BtII promoter, a bacterial STAB-SD sequence, and a sequence encoding proteins of the *B. sphaericus* ("Bs") binary toxin and expressed in *B. thuringiensis* ("Bt") or Bs cells results in production of Bs binary toxin at least 10 times that of untransformed Bs cells. The invention provides nucleic acid sequences, expression vectors, host cells, and methods of increasing the toxicity of an insecticidal bacterium by transforming the bacterium with a nucleic acid sequence of the invention. Further, the invention relates to the discovery that the Cyt1Aa1 protein of Bt subspecies *israelensis* ("Bti") reverses resistance to Bs binary toxin in Bs-resistant mosquitoes. The invention provides Bs cells expressing Bti Cyt1Aa1 protein, and methods of reversing resistance to Bs binary toxin by co-administering the Cyt1Aa1 protein with Bs binary toxin.

37 Claims, 5 Drawing Sheets

OTHER PUBLICATIONS

Servant, P. "Production of Cry11A and Cry11a Toxins in *Bacillus sphaericus* Confers Toxicity towards *Aedes aegypti* and Resistant *Culex* Populations," *Applied and Environmental Microbiology*, 65(7):3021–3026 (Jul. 1999).

Thiery, I. et al., "The Introduction into *Bacillus sphaericus* of the *Bacillus thuringiensis* subsp. *medellin* cyt1AB1 Gene Results in Higher Susceptibility of resistant Mosquito Larva Populations to *Bacillus sphaericus*," *Applied and Environmental Microbiology*, 64(10):3910–3916 (Oct. 1998).

Wirth, M. et al., "Cyt1A from *Bacillus thuringiensis* Synergizes Activity of *Bacillus sphaericus* against *Aedes aegypti* (Diptera: Cluicidae)," *Applied and Environmental Microbiology*, 66(3):1093–1097 (Mar. 2000).

Wirth, M. et al., "Cyt1A from *Bacillus thuringiensis* Restores Toxicity of *Bacillus sphaericus* Against Resistant *Culex quinquefasciatus* (Diptera: Culicidae)," *J. Med. Entomol.* 37(3):401;407 (2000).

* cited by examiner

```
          10        20        30        40        50        60
           *         *         *         *         *         *
GAATTCTATTTTCGATTTCAAATTTTCCAAACTTAAATATGATTGAATGCCTGAGAAAGG 70        80        90       100       110       120
           *         *         *         *         *         *
TAATAGAGATGTTTTAGTTTATTATGAAGTATTAGGGGCGTCTTTTAAATTCAATCTATC 130       140       150       160       170       180
           *         *         *         *         *         *
AATTTGTGAAATATATTACTCAAAACCCAATACCATTCTAAAACTTATTCAAAATATATA 190       200       210       220       230       240
           *         *         *         *         *         *
                                    -35      SIGMA E    -10
TTGCTTTAAAAGAGCATACATACTAAAAAAACAGGCATCTTTCGAACTATAGCGCATAGA 250       260       270       280       290       300
           *         *         *         *         *         *
ATACTACGGTGAATCAAAAACAAATAAAATTTAGGAGGTATATTCAAGTATACAAAAAAA 310       320       330       340       350       360
           *         *         *         *         *         *
CTTTAGTGTGAGGGGATTTAGATAAAAGTATTCGTTATCCTTATAAATTAATTCTTAAA 370       380       390       400       410       420
           *         *         *         *         *         *
  -35    SIGMA K   -10
CATGCACCAATGTATACATTAAATAATATTATGTGAATTAAGTCTATCAATTTAATTTAT 430       440       450       460       470       480
           *         *         *         *         *         *
TATGTTACTTTATATTTGATTAATAATTGCAAGTTTAAAATCATAATTTAATGTTGAAAG 490       500       510       520       530       540
           *         *         *         *         *         *
GCCACTATTCTAATTAACTTAAGGAGTTGTTTATTTGAGCTCGGTACCCGGGGATAAtct 550       560       570       580       590       600
           *         *         *         *         *         *
 STAB-SD
tGAAAGGAGGgatgcctaaaaacgaagaacattaaaaacatatatttgcaccgtctaatg 610       620       630       640       650       660
           *         *         *         *         *         *
gatttatgaaaaatcattttatcagtttgaaaattatgtattatgataagaaagtctagA 670       680       690       700       710       720
           *         *         *         *         *         *
ACGTTATTTAATGAACTTTTTAGGTTTTAAATAATATAATGAGAAGTATTTTTTATCAAT 730       740       750       760       770       780
           *         *         *         *         *         *
  RBS                 +1
GATAAGGAGATGAAGAAAGCATGTGCGATTCAAAAGACAATTCTGGCGTTTCAGAAAAAT
                     MetCysAspSerLysAspAsnSerGlyValSerGluLys>
                    [ 51.4 kilodalton protein  >>

790       800       810       820       830       840
           *         *         *         *         *         *
GCGGAAAGAAATTTACTAATTACCCGCTAAATACTACTCCTACAAGCCTAAATTATAACC
CysGlyLysLysPheThrAsnTyrProLeuAsnThrThrProThrSerLeuAsnTyrAsn>
```

Fig. 1A

```
        850       860       870       880       890       900
         *         *         *         *         *         *
TTCCAGAAATATCAAAAAAATTTTATAACCTTAAGAATAAATATTCACGGAATGGTTATG
LeuProGluIleSerLysLysPheTyrAsnLeuLysAsnLysTyrSerArgAsnGlyTyr>

910       920       930       940       950       960
         *         *         *         *         *         *
GTTTATCAAAAACCGAATTTCCTTCAAGTATCGAAAATTGCCCATCTAACGAATATTCAA
GlyLeuSerLysThrGluPheProSerSerIleGluAsnCysProSerAsnGluTyrSer>

970       980       990      1000      1010      1020
         *         *         *         *         *         *
TAATGTATGATAATAAAGATCCTCGATTCTTGATTCGGTTTTTATTAGATGATGGTAGAT
IleMetTyrAspAsnLysAspProArgPheLeuIleArgPheLeuLeuAspAspGlyArg>

1030      1040      1050      1060      1070      1080
         *         *         *         *         *         *
ATATTATTGCAGATAGAGACGATGGAGAAGTTTTTGATGAAGCACCTACTTATTTGGATA
TyrIleIleAlaAspArgAspAspGlyGluValPheAspGluAlaProThrTyrLeuAsp>

1090      1100      1110      1120      1130      1140
         *         *         *         *         *         *
ATAACAATCACCCTATCATAAGTAGACATTATACCGGAGAAGAGAGACAAAAGTTTGAGC
AsnAsnAsnHisProIleIleSerArgHisTyrThrGlyGluGluArgGlnLysPheGlu>

1150      1160      1170      1180      1190      1200
         *         *         *         *         *         *
AGGTAGGTAGTGGAGATTATATTACGGGAGAGCAATTTTTTCAATTCTATACACAAAACA
GlnValGlySerGlyAspTyrIleThrGlyGluGlnPhePheGlnPheTyrThrGlnAsn>

1210      1220      1230      1240      1250      1260
         *         *         *         *         *         *
AAACACGTGTATTGTCAAATTGTAGGGCGCTTGACAGTAGGACAATATTACTATCTACTG
LysThrArgValLeuSerAsnCysArgAlaLeuAspSerArgThrIleLeuLeuSerThr>

1270      1280      1290      1300      1310      1320
         *         *         *         *         *         *
CAAAAATCTTCCCAATTTACCCTCCAGCTTCTGAAACTCAACTAACAGCTTTCGTTAATA
AlaLysIlePheProIleTyrProProAlaSerGluThrGlnLeuThrAlaPheValAsn>

1330      1340      1350      1360      1370      1380
         *         *         *         *         *         *
GTTCATTTTATGCTGCGGCAATTCCTCAATTACCCCAAACATCCTTACTTGAGAATATTC
SerSerPheTyrAlaAlaAlaIleProGlnLeuProGlnThrSerLeuLeuGluAsnIle>

1390      1400      1410      1420      1430      1440
         *         *         *         *         *         *
CTGAGCCTACTAGTCTCGATGATTCTGGAGTATTACCAAAAGATGCAGTAAGAGCAGTTA
ProGluProThrSerLeuAspAspSerGlyValLeuProLysAspAlaValArgAlaVal>

1450      1460      1470      1480      1490      1500
         *         *         *         *         *         *
AAGGAAGTGCGCTATTACCTTGTATAATAGTACATGATCCTAATTTAAACAATTCCGATA
LysGlySerAlaLeuLeuProCysIleIleValHisAspProAsnLeuAsnAsnSerAsp>

1510      1520      1530      1540      1550      1560
         *         *         *         *         *         *
AAATGAAATTTAATACCTACTATCTTTTAGAATATAAGAATACTGGCATCAATTATGGT
LysMetLysPheAsnThrTyrTyrLeuLeuGluTyrLysGluTyrTrpHisGlnLeuTrp>

1570      1580      1590      1600      1610      1620
         *         *         *         *         *         *
CACAAATTATACCTGCTCATCAAACTGTAAAAATACAGGAACGAACAGGAATATCTGAAG
```

Fig. 1B

```
          SerGlnIleIleProAlaHisGlnThrValLysIleGlnGluArgThrGlyIleSerGlu>
        1630      1640      1650      1660      1670      1680
          *         *         *         *         *         *
     TTGTACAAAATAGCATGATTGAAGATTTAAATATGTATATTGGAGCAGATTTTGGCATGC
     ValValGlnAsnSerMetIleGluAspLeuAsnMetTyrIleGlyAlaAspPheGlyMet>

1690      1700      1710      1720      1730      1740
          *         *         *         *         *         *
     TTTTTTATTTTAGATCTAGTGGATTTAAGGAACAAATAACAAGGGGGCTAAATAGGCCTT
     LeuPheTyrPheArgSerSerGlyPheLysGluGlnIleThrArgGlyLeuAsnArgPro>

1750      1760      1770      1780      1790      1800
          *         *         *         *         *         *
     TATCCCAAACGACCACTCAGTTAGGAGAAAGAGTAGAAGAAATGGAGTATTATAATTCTA
     LeuSerGlnThrThrThrGlnLeuGlyGluArgValGluGluMetGluTyrTyrAsnSer>

1810      1820      1830      1840      1850      1860
          *         *         *         *         *         *
     ATGATTTGGATGTTAGATATGTGAAATACGCATTGGCTAGAGAATTCACACTAAAACGCG
     AsnAspLeuAspValArgTyrValLysTyrAlaLeuAlaArgGluPheThrLeuLysArg>

1870      1880      1890      1900      1910      1920
          *         *         *         *         *         *
     TTAATGGTGAAATTGTAAAAAATTGGGTTGCTGTAGATTATCGATTGGCAGGTATACAAT
     ValAsnGlyGluIleValLysAsnTrpValAlaValAspTyrArgLeuAlaGlyIleGln>

1930      1940      1950      1960      1970      1980
          *         *         *         *         *         *
     CGTATCCTAATGCACCTATAACTAATCCACTTACGCTAACAAAACATACAATTATTCGAT
     SerTyrProAsnAlaProIleThrAsnProLeuThrLeuThrLysHisThrIleIleArg>

1990      2000      2010      2020      2030      2040
          *         *         *         *         *         *
     GTGAAAATAGTTACGATGGACACATATTTAAAACACCTTTAATCTTTAAAAATGGTGAAG
     CysGluAsnSerTyrAspGlyHisIlePheLysThrProLeuIlePheLysAsnGlyGlu>

2050      2060      2070      2080      2090      2100
          *         *         *         *         *         *
     TTATTGTAAAAACGAATGAAGAATTAATACCTAAAATTAACCAGTGATACTTTAACTTCA
     ValIleValLysThrAsnGluGluLeuIleProLysIleAsnGlnStop
         > End 51.4 kilodalton protein]

2110      2120      2130      2140      2150      2160
          *         *         *         *         *         *
     AATATTCATTACCATGTTATTTAAAATAGTAGATAGATGAAATAAATAGTATATATTAAG 2170      2180      2190      2200      2210      2220
          *         *         *         *         *         *
     ACAACAACTTAATTTTGACACATAAGAATAATTTTTAAATGTATAAATAGTATTTAGAGT 2230      2240      2250      2260      2270      2280
          *         *         *         *         *         *
                              RBS         +1
     GTTATTGCAATATATTTTTTGAAAGGGAGCTAAAAGACATGAGAAATTTGGATTTTATTG
                                            MetArgAsnLeuAspPheIle>
                                            [ 41.9 kilodalton 2290      2300      2310      2320      2330      2340
          *         *         *         *         *         *
     ATTCTTTTATACCCACAGAAGGAAAGTACATTCGCGTTATGGATTTTTATAATAGCGAGT
     AspSerPheIleProThrGluGlyLysTyrIleArgValMetAspPheTyrAsnSerGlu>
     protein >
```

Fig. 1C

```
         2350        2360        2370        2380        2390        2400
           *           *           *           *           *           *
     ATCCTTTCTGTATACATGCACCCTCAGCCCCTAATGGGGATATCATGACAGAAATCTGTA
     TyrProPheCysIleHisAlaProSerAlaProAsnGlyAspIleMetThrGluIleCys>

2410        2420        2430        2440        2450        2460
           *           *           *           *           *           *
     GCAGAGAAAATAATCAATATTTTATTTTTTTTCCTACTGATGATGGTCGAGTAATTATTG
     SerArgGluAsnAsnGlnTyrPheIlePhePheProThrAspAspGlyArgValIleIle>

2470        2480        2490        2500        2510        2520
           *           *           *           *           *           *
     CAAATAGGCATAATGGGTCCGTTTTTACCGGAGAAGCCACAAGTGTAGTATCAGATATCT
     AlaAsnArgHisAsnGlySerValPheThrGlyGluAlaThrSerValValSerAspIle>

2530        2540        2550        2560        2570        2580
           *           *           *           *           *           *
     ATACTGGTAGCCCATTACAGTTTTTTAGAGAGGTCAAAAGAACTATGGCAACTTATTATT
     TyrThrGlySerProLeuGlnPhePheArgGluValLysArgThrMetAlaThrTyrTyr>

2590        2600        2610        2620        2630        2640
           *           *           *           *           *           *
     TAGCGATACAAAATCCTGAATCCGCAACAGATGTGAGAGCTCTAGAACCGCATTCCCATG
     LeuAlaIleGlnAsnProGluSerAlaThrAspValArgAlaLeuGluProHisSerHis>

2650        2660        2670        2680        2690        2700
           *           *           *           *           *           *
     AGCTGCCATCTCGCCTTTATTACACTAACAATATTGAAAATAATAGCAACATATTAATTT
     GluLeuProSerArgLeuTyrTyrThrAsnAsnIleGluAsnAsnSerAsnIleLeuIle>

2710        2720        2730        2740        2750        2760
           *           *           *           *           *           *
     CTAATAAGGAACAAATATATTTAACCTTGCCTTCACTTCCAGAAAACGAGCAATACCCTA
     SerAsnLysGluGlnIleTyrLeuThrLeuProSerLeuProGluAsnGluGlnTyrPro>

2770        2780        2790        2800        2810        2820
           *           *           *           *           *           *
     AAACTCCAGTATTAAGCGGTATCGATGATATAGGACCTAATCAATCAGAGAAATCAATAA
     LysThrProValLeuSerGlyIleAspAspIleGlyProAsnGlnSerGluLysSerIle>

2830        2840        2850        2860        2870        2880
           *           *           *           *           *           *
     TAGGAAGTACTCTTATCCCATGTATAATGGTTTCGGATTTTATTAGTTTGGGGGAGAGAA
     IleGlySerThrLeuIleProCysIleMetValSerAspPheIleSerLeuGlyGluArg>

2890        2900        2910        2920        2930        2940
           *           *           *           *           *           *
     TGAAAACCACTCCATATTATTATGTAAAGCACACTCAATATTGGCAAAGCATGTGGTCCG
     MetLysThrThrProTyrTyrTyrValLysHisThrGlnTyrTrpGlnSerMetTrpSer>

2950        2960        2970        2980        2990        3000
           *           *           *           *           *           *
     CGCTCTTTCCACCCGGCTCTAAAGAGACAAAAACTGAGAAATCAGGTATCACTGACACTT
     AlaLeuPheProProGlySerLysGluThrLysThrGluLysSerGlyIleThrAspThr>

3010        3020        3030        3040        3050        3060
           *           *           *           *           *           *
     CTCAAATAAGTATGACTGACGGGATTAATGTTTCAATCGGAGCAGATTTCGGATTAAGGT
     SerGlnIleSerMetThrAspGlyIleAsnValSerIleGlyAlaAspPheGlyLeuArg>

```
TTGGAAATAAAACGTTTGGAATTAAGGGGGGGTTCACCTATGATACAAAGACTCAAATAA
PheGlyAsnLysThrPheGlyIleLysGlyGlyPheThrTyrAspThrLysThrGlnIle>

3130      3140      3150      3160      3170      3180
         *         *         *         *         *         *
CTAATACCTCCCAATTGTTAATAGAAACAACTTATACTAGAGAATACACAAATACAGAAA
ThrAsnThrSerGlnLeuLeuIleGluThrThrTyrThrArgGluTyrThrAsnThrGlu>

3190      3200      3210      3220      3230      3240
         *         *         *         *         *         *
ATTTTCCTGTTAGATATACAGGCTATGTTTTAGCGTCAGAATTTACTTTACATCGTAGTG
AsnPheProValArgTyrThrGlyTyrValLeuAlaSerGluPheThrLeuHisArgSer>

3250      3260      3270      3280      3290      3300
         *         *         *         *         *         *
ATGGAACTCAGGTTAATACGATCCCATGGGTTGCTTTAAACGATAACTATACAACAATAG
AspGlyThrGlnValAsnThrIleProTrpValAlaLeuAsnAspAsnTyrThrThrIle>

3310      3320      3330      3340      3350      3360
         *         *         *         *         *         *
CAAGATATCCACATTTTGCAAGTGAACCTTTACTAGGAAATACAAAGATTATTACAGATG
AlaArgTyrProHisPheAlaSerGluProLeuLeuGlyAsnThrLysIleIleThrAsp>
                                              > end 41.9 kilodalton 3370      3380      3390      3400      3410      3420
         *         *         *         *         *         *
ATCAAAACTAAATTTAAACAATATTCTTGAACTAATAGATGTTAAATAGAACAATTAATA
AspGlnAsnStop
protein  ]

3430      3440      3450      3460      3470      3480
         *         *         *         *         *         *
ACAATTTAAGTACTTTTGGATTATAGTGAAGGGACCTATAAGCATAGCTTTTAGGTCCCT 3490      3500      3510      3520      3530      3540
         *         *         *         *         *         *
TTTAAGTTGCTTTTTTTCGTTTTTAGAATAGTATAGATAGGCTACACTACACTAAGTTGG 3550      3560      3570      3580      3590      3600
         *         *         *         *         *         *
ACAGATAAAATAAGGGGTTGTAAACTTAGACTATTAAAAAAGGGAGAGTGCTACTATGAC 3610      3620      3630      3640      3650
         *         *         *         *         *
ACGTCAACATCGAACTTTTACACTCGAATGTAAACTGTTGTTGTTTGGCTGCAG
```

Fig. 1E

INSECTICIDAL BACTERIA, AND METHODS FOR MAKING AND USING THEM

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Despite advances in medical science and new drugs, malaria, filariasis, dengue and the viral encephalilitides remain important diseases of humans, with an estimated 2 billion people worldwide living in areas where these are endemic (*The World Health Report*—1999, World Health Organization, Geneva, Switzerland (1999)). The causative agents of these diseases are transmitted by mosquitoes, and therefore disease control methods have relied heavily on broad spectrum chemical insecticides to reduce mosquito populations. However, chemical insecticide usage is being phased out in many countries due the development of insecticide resistance in mosquito populations. Furthermore, many governments restrict use of these chemicals because of concerns over their effects on the environment, especially on non-target beneficial insects, and vertebrates through contamination of food and water supplies.

As a result of these problems, the World Health Organization is facilitating the replacement of chemical with bacterial-based insecticides through the development of standards for their registration and use (Guideline specifications for bacterial larvicides for public health use, WHO Document WHO/CDS/CPC/WHOPES/99.2, World Health Organization, Geneva, Switzerland (1999)). Products based on bacteria have been designed to control mosquito larvae, and the two most widely used are Vectobac® and Teknar®, both of which are based on *Bacillus thuringiensis* subsp. *israelensis*. In addition, Vectolex®, a new product based on *B. sphaericus* has come to market recently for control of the mosquito vectors of filariasis and viral diseases. These products have achieved moderate commercial success, but their high cost and lower efficacy compared to many chemical pesticides prevents them from being used more extensively in many developing countries. Moreover, concerns have been raised about their long term utility due to resistance, which has already been reported to *B. sphaericus* in field populations of Culex mosquitoes in India, Brazil, and France (Sinègre, et al. First field occurrence of Culex pipiens resistance to *Bacillus sphaericus* in southern France, VII European Meeting, Society for Vector Ecology, 5–8 September Barcelona, Spain (1994); Rao et al.,*J. Am. Mosq. Control Assoc.* 11:1–5 (1995); Silva-Filha et al., *J. Econ. Entomot* 88: 525–530 (1995)).

The insecticidal properties of these bacteria are due primarily to insecticidal proteins produced during sporulation. In *Bacillus thuringiensis* subsp. *israelensis* (Bti), the key proteins are Cyt1A (27 kDa), Cry11A (72 kDa), Cry4A (128 kDa) and Cry4B (134 kDa), whereas *B. sphaericus* (Bs) produces 41- and 52-kDa proteins that serve, respectively, as the toxin and binding domains of a single binary toxin (Federici et al. in *Bacterial Control of Mosquitoes and Blackflies*, eds.: de Barjac & Sutherland, D. J, 11–44 (Rutgers University Press, New Brunswick, N.J.) (1990); Baumann et al., *Microbiol. Rev.* 55:425–436 (1991)).

Biochemical and toxicological differences in the Bti and Bs toxins suggested that it might be possible to construct an improved bacterium by combining their toxins into a single bacterium. Numerous attempts using this approach have been made over the past decade to create a recombinant bacterium with the desired toxicity. Several groups, for example, have introduced Bti toxin genes in Bs. For example, Bar et al., *J. Invertebrate Pathol.* 149–158 (1991 cloned Bti endotoxin genes into Bs 2362, but found that the biological activity of the recombinant organism was lower than that of Bti. Poncet et al., *FEMS Microbiol Lett.* 117:91–96 (1994) cloned the cry4B and cry11A genes of Bti into Bs 2297, and Poncet et al., *Appl Environ, Microbiol.* 63:4413–4420 (1997) introduced the cry11A gene into the same strain by homologous recombination. Thoéry et al., *Appl. Environ. Microbiol.* 64:3910–3916 (1998) introduced a Bt cyt1Ab1 gene into Bs, but reported that the level of expression of the cyt1Ab1 gene was probable too low to have any significant effect on toxicity. Servant et al., Appl Environ Microbiol. 65:3021–3026 (1999) introduced Cry11A and Cry11Ba Bt toxins in Bs 2297 by in vivo recombination, and showed that the host range could thereby be increased. Bourgouin et al., *Appl. Environ Microbiol.* 56:340–344 (1990) introduced Bs toxin into Bti, but found no synergistic or additive effect between the toxins against mosquito larvae. Attempts to combine the advantages of Bs and Bt in other manners have also apparently not proven commercially useful. Simply growing cultures of Bs and Bt and then combining the two organisms, for example, is not effective because the spores of the two organisms are considered to form too large a proportion of the resulting mix in proportion to the weight of the toxins to provide adequate toxicity.

Commercial development of new biopesticides is costly, in part because of EPA regulations requiring extensive testing, and margins are low relative to, for example, pharmaceutical agents. It does not appear that any of the recombinant organisms reported in the past decade have shown sufficient improvement over current commercial Bti or Bs strains to warrant development for commercial use in mosquito control.

SUMMARY OF THE INVENTION

The invention provides nucleotide sequences, expression vectors, host cells and methods for achieving the high level expression of Bs binary toxin, particularly in cells of Bacillus species and especially in Bs and in Bt cells.

In particular, the invention provides nucleic acid sequences comprising, in the following order, A nucleic acid sequence comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin. In some embodiments, the bacterial STAB-SD sequence is selected from the group consisting of GAAAGGAGG (SEQ ID NO:1), GAAGGGGGG (SEQ ID NO:2), GAGGGGGGG (SEQ ID NO:3), GAAAGGGGG (SEQ ID NO:4), GAAAGGAGG (SEQ ID NO:5), and GAAAGGGGT (SEQ ID NO:6). The *B. thuringiensis* promoter is a cry promoter, and in particular can be a cry1 promoter.

Further, the *B. thuringiensis* promoter can be cry1Aa1, cry1Aa2, cry1Aa3, cry1Aa4, cry1Aa5, cry1Aa6, cry1Ba1, cry1Ba2, cry1Ca1, cry1Ca2, cry1Ca3, cry1Ca4, cry1Ca5, cry1Ca6, cry1Ca7 cry1Fa1, cry1Fa2, cyt1Aa1, cyt1Aa2, cyt1Aa3, or cyt1Aa4. In some preferred embodiments, the *B. thuringiensis* promoter is a cyt1Aa1 promoter. The nucleic acid can have both a BtI promoter and a BtII promoter, and the two promoters can be overlapping.

The invention further provides expression vectors comprising the nucleic acid described above, and host cells comprising the expression vectors. The host cells can further comprise a 20 kD protein encoded by the Bti cry11A operon. In preferred embodiments, the host cell is a *B. thuringiensis* cell or a *B. sphaericus* cell.

The invention further provides a nucleic acid sequence comprising, in the following order, a *B. thuringiensis* promoter which binds a sigma factor A protein, a bacterial STAB-SD sequence, a ribosome binding site, and a sequence encoding one or both proteins of a *B. sphaericus* binary toxin.

The invention also relates to a method of enhancing production of *B. sphaericus* binary toxin in a host bacterial cell, said method comprising: transforming the host cell with a gene comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin; and expressing said gene in the host cell; whereby expression of said gene enhances production of *B. sphaericus* binary toxin as compared to production of *B. sphaericus* binary toxin in a wild-type *B. sphaericus* cell that is not transformed with said gene. The bacterial STAB-SD sequence used in the method can be selected from the group consisting of GAAAGGAGG (SEQ ID NO:1), GAAGGGGGG (SEQ ID NO:2), GAGGGGGGG (SEQ ID NO:3), GAAAGGGGG (SEQ ID NO:4), GAAAGGAGG (SEQ ID NO:5), and GAAAGGGGT (SEQ ID NO:6). The host cell used in the method can be a *B. thuringiensis* cell or a *B. sphaericus* cell. The host cell may further express a 20 kD product of a cry11A gene.

In other embodiments, the invention relates to a method of creating a recombinant bacterium, said method comprising the steps of: transforming the recombinant bacterium with a gene comprising, in the following order: a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin; and expressing said gene in the host cell; whereby expression of said gene enhances production of *B. sphaericus* binary toxin as compared to production of *B. sphaericus* binary toxin in a wild-type *B. sphaericus* cell that is not transformed with said gene. The bacterial STAB-SD sequence used in the method can be selected from the group consisting of GAAAGGAGG (SEQ ID NO:1), GAAGGGGGG (SEQ ID NO:2), GAGGGGGGG (SEQ ID NO:3), GAAAGGGGG (SEQ ID NO:4), GAAAGGAGG (SEQ ID NO:5), and GAAAGGGGT (SEQ ID NO:6). The recombinant bacterium used in the method can be selected from the group consisting of *B. thuringiensis, B. sphaericus,* and a member of a Bacillus species other than Bti or Bs.

The invention also relates to a method of increasing toxicity of a *B. thuringiensis* bacterium to a mosquito, said method comprising the steps of: transforming said bacterium with a nucleic acid sequence comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins a *B. sphaericus* binary toxin; and expressing said gene in the bacterium; whereby expression of said gene enhances production of *B. sphaericus* binary toxin as compared to production of *B. sphaericus* binary toxin in a wild-type *B. sphaericus* cell that is not transformed with said gene. The bacterium can further comprise a 20 kD product of the cry11A gene.

In another group of embodiments, the invention provides a recombinant cell of *B. sphaericus*, said cell comprising nucleic acid sequence comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin. The bacterial STAB-SD sequence present in the recombinant cell can be selected from the group consisting of GAAAGGAGG (SEQ ID NO:1), GAAGGGGGG (SEQ ID NO:2), GAGGGGGGG (SEQ ID NO:3), GAAAGGGGG (SEQ ID NO:4), GAAAGGAGG (SEQ ID NO:5), and GAAAGGGGT (SEQ ID NO:6). The *B. thuringiensis* promoter can be a cry promoter, or can be selected from the group consisting of cry1Aa1, cry1Aa2, cry1Aa3, cry1Aa4, cry1Aa5, cry1Aa6, cry1Ba1, cry1Ba2, cry1Ca1, cry1Ca2, cry1Ca3, cry1Ca4, cry1Ca5, cry1Ca6, cry1Ca7cry1Fa1, cry1Fa2, cyt1Aa1, cyt1Aa2, cyt1Aa3, and cyt1Aa4. In a preferred embodiment, the *B. thuringiensis* promoter is a cyt1Aa1 promoter. The recombinant cell can further express a 20 kD product of a cry11A operon.

In yet another set of embodiments, the invention provides a method for increasing toxicity of a *B. sphaericus* cell, said method comprising transforming the cell with a nucleic acid sequence comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin; and expressing said nucleic acid sequence in the host cell; whereby expression of said nucleic acid sequence enhances production of *B. sphaericus* binary toxin as compared to production of *B. sphaericus* binary toxin in a wild-type *B. sphaericus* cell that is not transformed with said nucleic acid sequence. The bacterial STAB-SD sequence can be selected from the group consisting of GAAAGGAGG (SEQ ID NO: 1), GAAGGGGGG (SEQ ID NO:2), GAGGGGGGG (SEQ ID NO:3), GAAAGGGGG (SEQ ID NO:4), GAAAGGAGG (SEQ ID NO:5), and GAAAGGGGT (SEQ ID NO:6). The *B. thuringiensis* promoter can be a cry promoter, or can be selected from the group consisting of cry1Aa1, cry1Aa2, cry1Aa3, cry1Aa4, cry1Aa5, cry1Aa6, cry1Ba1, cry1Ba2, cry1Ca1, cry1Ca2, cry1Ca3, cry1Ca4, cry1Ca5, cry1Ca6, cry1Ca7 cry1Fa1, cry1Fa2, cyt1Aa1, cyt1Aa2, cyt1Aa3, and cyt1Aa4. In a preferred embodiment, the *B. thuringiensis* promoter is a cyt1Aa1 promoter.

The invention also provides a method for suppressing resistance to a *B. sphaericus* binary toxin, said method comprising expressing a Bti Cyt1Aa1 protein in a *B. sphaericus* cell expressing said binary toxin, as well as a method for suppressing resistance to a *B. sphaericus* binary toxin, the method comprising expressing a Bti Cyt1Aa1 protein in a *B. thuringiensis* cell expressing said binary toxin. In yet another embodiment, the invention provides a method for suppressing resistance to a *B. sphaericus* binary toxin, the method comprising administering Bti Cyt1Aa1 protein with said binary toxin. The Bti Cyt1Aa1 protein can be in a powder of lysed, lyophilized Bti cells, or can be in the form of a purified protein. The Bti Cyt1Aa1 protein is administered in a Cyt1Aa1 protein to Bs ratio selected from about 1:2 to about 1:50. In especially preferred embodiments, the Bti Cyt1Aa1 protein is administered in a Cyt1Aa1 protein to Bs ratio of about 1:10.

BRIEF DESCRIPTION OF THE DRAWINGS

FIG. 1 sets forth the nucleotide sequence (SEQ ID NO:7) and encoded amino acid sequence of a fragment used to clone Bs binary toxin into a plasmid. "Sigma E" and Sigma K" denote the binding sites for sigma factors E and K, respectively. The underlined sequence between nucleotides 537 and 660 denotes a portion cloned into the sequence by PCR to introduce a STAB-SD sequence, which is denoted both by capital letters in the underlined portion, and the "STAB-SD superscript. The start and stop codons of the 51.4 kD protein (SEQ ID NO:8) and of the 41.9 kD protein (SEQ ID NO:9) are noted. The underlined sections between nucleotides 725 and 730, and between 2245 and 2250, marked "RBS," represents the ribosome binding site.

DETAILED DESCRIPTION

I. Introduction

The inventions provides nucleic acid sequences, vectors, host cells, and methods for obtaining high levels of synthesis of the binary toxin of *Bacillus sphaericus* ("Bs") in recombinant bacterial cells. Bs toxin is very potent, but is produced by wild-type Bs cells at low levels. This, coupled with it being only a single toxin (in contrast, for example, to Bt, which produces a complex of toxins), permits the rapid development of insects resistant to the toxin. Increasing the amount of toxin produced per cell increases the killing power of the resultant biopesticide formulation and decreases the possibility that larvae ingesting the biopesticide will survive. Moreover, the increase in amount of toxin per cell greatly increases the efficiency of the bacterial toxin fermentation production process, and reduces the amount of bacterial product that must be applied to achieve insect control. Thus, the invention markedly reduces the cost of production and use and makes biopesticides more competitive with chemical pesticides, which can be effective, but which are more environmentally damaging.

The nucleic acids of the invention are heterologous sequences made by inserting a STAB-SD nucleic acid sequence between a strong promoter from a Bt gene and the ribosome binding site, and combining this construct with a nucleic acid sequence encoding the binding protein of the *BS* toxin, or the toxin protein, or both. In preferred embodiments, both proteins are present. Surprisingly, coupling a strong Bt promoter with the STAB-SD nucleic acid sequence results in a dramatic increase in the production of the Bs toxin, by at least 10, and usually 15 to 20, times over the amount of protein produced by standard strains of unaltered (wild-type) *B. sphaericus*. The presence of the Bs binary toxin, in turn, results in surprising increases in the toxicity of the recombinant cells. For example, the toxicity of recombinant cells against the larvae of mosquitoes of the genus Culex is increased by more than 10 fold compared to non-recombinant cells.

Optionally, the recombinant cell further contains a 20 kD chaperone-like product of a cry11A operon. Surprisingly, the presence of this protein increases the synthesis of Bs protein from the nucleic acid sequence described above by an additional 50% to 100%, and thus increases production of the Bs toxin to some 20 to 30 times more than that produced by standard strains of *Bs*.

Due to the costs of obtaining regulatory approval for new pesticides and the like, it is generally desirable that the toxicity of the bacterial cells be increased by at least about 5 times against an organism of interest to warrant investment. Efforts by others for more than a decade to produce Bs toxin in Bs and *Bacillus thuringiensis* ("Bt") have resulted in increases in amounts of toxin production of 2, 3, or 4-fold, too modest to be of interest for commercial production or for field use. Thus, the ability of the invention to permit production of Bs toxin in amounts that are at least 10, more usually 15, and as much as 20, 25 or even 30 times as high as that produced in standard strains of Bs is a significant and surprising advance in the art. Equally surprisingly, in tests against Culex mosquitoes, a significant vector of human disease, the toxicity of Bt cells transformed with the nucleic acids of the invention was improved by at least 10 fold, without diminishing the toxicity of the cells to other genera of mosquitoes.

Biopesticides such as Bt are produced commercially in bioreactors. The ability provided by the invention to increase the toxicity of bacterial cells such as Bt or Bs means the amount of toxin produced per unit of culture medium will be increased, permitting the culturing of smaller quantities, and a commensurately decrease in the of raw materials used for the culture medium. Thus, the invention reduces the cost of producing biopesticides, which will extend the situations in which it is cost-effective to use them in place of chemical pesticides. Moreover, the invention also provides the ability to confer Bs toxin-based toxicity on normally non-toxic bacterial species, and especially on species of bacillus which are normally non-toxic to insect larvae. Since the attributes of these other bacterial species, such as persistence in particular environments, are likely to be different than of the Bt and Bs which thus far have served as biopesticides, the invention also provides biopesticides with a different range of attributes than those currently available. The invention thereby expands the range of options for public health officials and agricultural scientists in combating insect pests.

The ability to produce high levels of Bs toxin is particularly useful to increase the toxicity of Bt subspecies, such as subsp. *israelensis*, which is useful to control dipteran pests such as mosquito and blackfly larvae (this strain of Bt is hereafter referred to as "Bti"), subsp. *kurstaki*, which is currently useful in controlling caterpillar pests, including, e.g., the corn earworm (*Heliothis zia*), the cabbage looper (*Trichoplusia ni*), and the fall army worm (*Spodoptera frugiperda*), and subsp. *morrisoni*, which is active, e.g., against coleopteran pests such as the Colorado potato beetle (*Leptinotarsa decemlineata*), and the cottonwood leaf beetle (*Chrysomela scripta*), as well as subsp. *tenebrionis*, and subsp. *aizawai*.

Moreover, the invention permits the extension of the host range of the biopesticide (that is, it extends the organisms against which the biopesticide is toxic). Bs toxin is toxic primarily to larvae of Culex and Anopheles species, while Bti is more active against Culex and Aedes species. Thus, the expression of high levels of Bs toxin in Bti cells not only increases their toxicity to Culex, but also renders the cells more useful agents against Anopheles species. Since Anopheles species are a major vector of malaria, this increased host range alone makes the invention a major addition to the public health arsenal.

The invention further relates to the discovery that the Cyt1Aa1 (also known as "Cyt1A") protein of Bti can restore toxicity of Bs to mosquitoes that were highly resistant to Bs toxin. Other groups have previously shown that the mechanism of resistance to Bs is a loss of binding to receptors in the insect midgut. Without wishing to be bound by theory, it appears that Cyt1Aa1 allows insertion of the Bs toxin into the midgut microvillar membrane, restoring toxicity.

Working with a *Culex quinquefasciattis* population at least 30,000-fold resistant to *B. sphaericus* 2362, the strain used in commercial biopesticide formulations, combining Bti Cyt1Aa1 with *B. sphaericus* completely suppressed resistance. Some suppression of resistance has previously been shown with a different Cyt protein, Cyt1Ab from *B. thuringiensis* subsp. *medellin* ("Btm"). Thiery et al., Appl. Environ. Microbiol. 64: 3910–3916 (1998). Surprisingly, however, the suppression of resistance by Bti Cyt1A is several fold higher than that which was achieved with Btm Cyt1Ab. Moreover, since Bs 2362 is the strain commercially used and to which target mosquito populations have already developed significant resistance, it is particularly important to suppress resistance to this strain. Thus, the discovery that Bti Cyt1Aa1 protein restores toxicity to Bs 2362 offers a solution to a major problem which has discouraged the continued use of Bs as a biopesticide. We reported these results in Wirth et al., J. Med. Entomol. 37:401–407 (2000).

This discovery can be exploited by producing Bti Cyt1Aa1 in a bacterial cell producing Bs toxin, such as a Bs cell or a Bt cell recombinantly altered to produce Bs toxin. If the Bs toxin is produced in a Bs cell recombinantly altered to express Bti Cyt1Aa1, it is preferred to also transform the cell to express the 20 kD chaperone-like protein encoded by the cry11A operon. The sequence of cyt1Aa1 is available from GenBank under accession number X03182, and was published by Waalwijk et al., Nucl. Acids Res. 13:8207–8217 (1985). The cry11A operon and the encoded 20 kD protein are discussed further below.

Alternatively, Bti Cyt1Aa protein or Bti cells producing Cyt1Aa (or cells of other Bacillus species recombinantly altered to produce Bti Cyt1Aa) can be added to cells, granules or powder produced from Bs to render the granules toxic to organisms which would otherwise be resistant.

As shown in the Examples, below, relatively modest amounts of Cyt1Aa1 protein are sufficient to dramatically suppress or even to eliminate resistance. In preferred embodiments, the Cyt1Aa1 protein can be added to a Bs mixture in a ratio selected from 1:2, 1:3, 1:4, 1:5, 1:6, 1:7, 1:8, 1:9 or 1:10, with 1:10 being the most preferred since it affords striking reversal of resistance with relatively low amounts of added material. Higher ratios, such as 1:12, 1:15, 1:20, 1:25, 1:30, 1:35, 1:40, 1:45, 1:50, 1:55, 1:60, 1:65, or 1:70 can also be employed if, for example, it is desired to reduce the cost of adding Cyt1Aa1 protein, with the understanding that lower ratios may provide somewhat lower suppression of resistance. The assays taught in Example 5 can be used to test any particular ratio to discern if it would provide the degree of reversal of resistance desired. Ratios of Cyt1Aa1 to Bs of less than 1:100 are not preferred.

The Cyt1Aa protein can be added as purified granules; however, it is usually easier to add Cyt1Aa in the form of Cyt1Aa-producing Bti cells. Conveniently, the Bti cells are lysed and lyophilized to form a powder prior to mixing with the Bs. In preferred embodiments, the Bs is strain 2362.

Based on our results, other Cyt1 proteins from Bti will work in the same manner to reverse resistance to Bs binary toxin.

Persons of skill in the art are aware that Bs and Bt cells are generally not administered together. Without wishing to be bound by theory, this may be due to concerns that the weight of the spores produced by each species relative to the toxin may reduce the effective amount of toxin the target larvae can ingest. The modest amounts of Bti which need to be added to achieve suppression of resistance, however, remove this concern as a factor. The studies reported in the Examples show ample toxicity when Bti cells were mixed with Bs.

Bt has been used commercially as a biopesticide for some 20 years, and Bs has been used commercially for some 5 years. The use of Bti and Bs in the field has been reviewed, for example, in Mulla, M. S., "Activity, field efficacy, and use of *Bacillus thuringiensis israelensis* against mosquitoes," pp. 134–160 and in Yap, H.-H., "Field trials of *Bacillus sphaericus* for mosquito control" pp. 307–320, in H. de Badac and D. J. Sutherland. [eds.] *Bacterial control of mosquitoes and blackflies*. Rutgers University Press (New Brunswick, N.J., 1990). Persons of skill in the art are therefore familiar with growing large quantities of Bt and of Bs organisms, with formulating biopesticides from those organisms, and with applying the formulations in the field. The recombinant organisms and methods described herein can be used in any of the methods known in the art for formulating biopesticides from Bt and Bs cells.

Recombinant Bs cells of the invention can be used in any of the methods in which Bs biopesticides are currently used, but can be applied at lower application rates proportionate to their increased toxicity compared to the strain currently used commercially. For example, if the recombinant Bs has a toxicity 10 times that of the current strain, then one-tenth the weight of the material currently used can be applied to obtain the same killing power. Moreover, recombinant cells which express Cyt1Aa1 can be used against mosquito populations which have become resistant to wild-type Bs binary toxin.

Recombinant Bt cells of the invention producing Bs binary toxin can be used to control the organisms normally controlled by Bt, and in addition can be used against Anopheles species. As discussed in connection with recombinant Bs, above, recombinant Bt expressing high levels of Bs toxin can be applied at lower application rates proportionate to the increased toxicity of the recombinant to the target organism compared to the strain currently used commercially. Thus, the invention permits the use of less material. Since reducing the amount of Bt or Bs means that less Bt or Bs has to be grown, less raw material is needed to produce the same amount of killing power and thus the net cost of producing enough material to treat a given amount of area is decreased.

The sections below define terms used in this specification. They then discuss Bt and Bs bacteria and their toxins, Bt promoters suitable for use in the invention, STAB-SD sequences, the assembly of nucleic acid sequences of the invention, and the 20 kD chaperone-like protein, as well as making and using the nucleic acids, vectors, host cells and bacteria of the invention.

II. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular*

*Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

"*Bacillus thuringiensis,*" "*B. thuringiensis,*" and "Bt" refer to a gram positive soil bacterium characterized by its ability to produce crystalline inclusions during sporulation. The inclusions include insecticidal endotoxins. The inclusions comprise insecticidal proteins (sometimes referred to as "crystal proteins") encoded by genes carried on plasmids. The bacteria can be "cured" of the plasmid by growing them at raised temperatures, resulting in cells which do not produce the crystal proteins. Such bacteria are referred to as "acrystalliferous" or "crystal minus" cells.

"*Bacillus sphaericus,*" or "Bs" refers to a gram positive soil bacterium which also produces a parasporal crystal of proteins toxic to certain insects.

"Binary toxin" refers to the toxin produced by Bs. The toxin is comprised of two proteins, one of which serves as a binding moiety and one of which serves as the toxin. The two proteins are capable of associating in a solution to form a functional toxin.

"Cry" and "Cyt" refer to members of two families of proteins produced by *B. thuringiensis*. The nomenclature in the art has recently changed from referring to the various Cry proteins by Roman numerals (intended to denote the apparent ranges of organisms to which the proteins are toxic) to Arabic numerals; the Cyt proteins were also redesignated. A comprehensive table correlating the nomenclature of the older designations and the current designations for some 130 Cry and Cyt proteins is set forth in Crickmore et al., Microbiol. Mol. Biol. Rev. 62:807–813 (1998).

The protein now termed "Cyt1Aa1" was sometimes previously referred to as "CytA" or "Cyt1A;" references herein to CytA or to Cyt1A refer to Cyt1Aa1.

Following standard usage in the art, the use of the terms "Cry" or "Cyt" herein denote the protein, while the lowercase, italicized terms "cry" or "cyt" refer to the genes.

A "promoter" is an array of nucleic acid control sequences, e.g., the cry1Ac1 promoter from *B. thuringiensis*, that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription.

A "BtI" promoter refers to a promoter which is recognized by sigma factor-E. A "BtII promoter" refers to a promoter which is recognized by sigma factor K.

A "strong BtI or BtII promoter" refers to a promoter which, when operably linked to a nucleic acid sequence encoding a protein, and expressed in a Bt cell, results in the protein comprising 15% or more of the dry weight of the cell.

"Sigma factors" refer to proteins known to recognize particular sequences in DNA and which form part of a complex of proteins which facilitate the initiation of transcription of the DNA by RNA polymerase. As is known in the art, the sequence of the sigma factor proteins was determined from studies in *B. subtilis*, the proteins performing the same functions in other Bacillus species have about 80–95% sequence to the sigma factors of *B. subtilis*. Accordingly, the factors which in Bt perform the same role as the sigma factors of *B. subtilis* have slightly different sequences than those of the paradigm proteins of *B. subtilis*. The term "sigma factor" herein refers to proteins in Bt performing the same function as the sigma factors of *B. subtilis* and having about 80–95% or higher sequence homology to those proteins. To make the point that these proteins correspond, but are not necessarily identical in sequence to the *B. subtilis* proteins, they are also sometimes referred to herein as "sigma-like" factors or proteins.

"Polynucleotide" and "nucleic acid" refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, an cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium." The gene is then expressed in the recombinant host cell to produce, e.g., a "recombinant protein." A recombinant polynucleotide may serve a non-coding function (e.g., promoter, origin of replication, ribosome-binding site, etc.) as well.

A "heterologous polynucleotide sequence" or a "heterologous nucleic acid" is a relative term referring to a polynucleotide that is functionally related to another polynucleotide, such as a promoter sequence, in a manner so that the two polynucleotide sequences are not arranged in the same relationship to each other as in nature. Heterologous polynucleotide sequences include, e.g., a promoter operably linked to a heterologous nucleic acid, and a polynucleotide including its native promoter that is inserted into a heterologous vector for transformation into a recombinant host cell. Heterologous polynucleotide sequences are considered "exogenous" because they are introduced to the host cell via transformation techniques. However, the heterologous polynucleotide can originate from a foreign source or from the same source. Modification of the heterologous polynucleotide sequence may occur, e.g., by treating the polynucleotide with a restriction enzyme to generate a polynucleotide sequence that can be operably linked to a regulatory element. Modification can also occur by techniques such as site-directed mutagenesis.

The term "expressed endogenously" refers to polynucleotides that are native to the host cell and are naturally expressed in the host cell.

An "expression cassette" refers to a series of polynucleotide elements that permit transcription of a gene in a host cell. Typically, the expression cassette includes a promoter and a heterologous or native polynucleotide sequence that is transcribed. Expression cassettes may also include, e.g., transcription termination signals, polyadenylation signals, and enhancer elements.

The term "operably linked" refers to a functional relationship between two parts in which the activity of one part (e.g., the ability to regulate transcription) results in an action on the other part (e.g., transcription of the sequence). Thus, a polynucleotide is "operably linked to a promoter" when there is a functional linkage between a polynucleotide expression control sequence (such as a promoter or other transcription regulation sequences) and a second polynucleotide sequence (e.g., a native or a heterologous polynucleotide), where the expression control sequence directs transcription of the polynucleotide.

An "insecticidal endotoxin" refers to a family of genes encoding endotoxin proteins that exhibit insecticidal activity, also known as crystal proteins, e.g., Cry2A, Cry3A, Cry1B, Cry1C (see Hofte & Whiteley, *Microbiol. Rev.* 53: 242–255 (1989)). Such insecticidal endotoxins are produced by *Bacillus thuringiensis* and are toxic to insects, particularly insect larvae.

An "insecticidally effective amount" of an insecticidal endotoxin is a unit dose amount that provides insecticidal activity when applied to a plant, soil, or another "locus," e.g., site or location.

The "gene encoding the cry11A operon 20 kDa protein" (20 kDa protein gene) refers to the gene in the cry11A operon that encodes a protein of approximately kDa (as described in Frutos et al., *Biochem. Sys. and Ecol.* 19:599–609 (1991); see Frutos et al. FIG. 4 for nucleotide and amino acid sequence).

"Enhancing production" refers to an activity of a first protein, such as the cry11A operon 20 kDa protein, that increases the net amount of a second protein, such as an insecticidal endotoxin, in a host cell.

"Competent to express" refers to a host cell that provides a sufficient cellular environment for expression of endogenous and/or exogenous polynucleotides.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) ("Ausubel")).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The terms "stringent hybridization conditions" or "stringent conditions" refer to conditions under which a nucleic acid sequence will hybridize to its complement, but not to other sequences in any significant degree. Stringent conditions in the context of nucleic acid hybridizations are sequence dependent and are different under different environmental parameters. Longer sequences hybridize specifically at higher temperatures. An extensive guide to the hybridization of nucleic acids is found in Tijssen, *Laboratory Techniques in Biochemistry and Molecular Biology— Hybridization with Nucleic Acid Probes*, Part I, Chapter 2 "Overview of principles of hybridization and the strategy of nucleic acid probe assays," Elsevier, New York, (1993) (the entirety of Tijssen is hereby incorporated by reference). Very stringent conditions are selected to be equal to the $T_M$ point for a particular probe. Less stringent conditions, by contrast, are those in which a nucleic acid sequence will bind to imperfectly matched sequences.

Stringency can be controlled by changing temperature, salt concentration, the presence of organic compounds, such as formamide or DMSO, or all of these. The effects of changing these parameters are well known in the art. The effect on $T_m$ of changes in the concentration of formamide, for example, is reduced to the following equation: $T_m = 81.5 + 16.6 (\log Na^+) + 0.41 (\%G+C) - (600/\text{oligo length}) - 0.63 (\%\text{formamide})$. Reductions in Tm due to TMAC and the effects of changing salt concentrations are also well known. Changes in the temperature are generally a preferred means of controlling stringency for convenience, ease of control, and reversibility.

III. The Bti and BS Toxins

Bti and Bs are aerobic, gram positive sporeforming soil organisms which produce proteinaceous crystalline inclusions during sporulation. The crystals of Bt subspecies are toxic to the larvae of a wide variety of leipdopteran, coleopteran and dipteran species. The Introduction lists some of the insects against which different subspecies of Bt are currently used. Bt comprises about 90% of all biopesticides used. Agaisse and Lereclus. J. Bacteriol. 177:6027–6033 (1995).

The cry and cyt genes encode the various insecticidal proteins produced by Bt. A large number of these genes have been identified and sequenced and are well known in the art. For example, Crickmore et al., Microbiol Mol Biol Rev., 62:807–813 (1998) (the whole of Crickmore et al. is hereby incorporated by reference) provide a table setting forth the GenBank accession numbers for the sequences of over 120 Bt identified cry genes and 9 Bt cyt genes.

As might be expected from the name, the binary toxin of Bs is composed of two proteins, one of 51.4 kD and one of 41.9 kD. The nucleotide and amino acid sequences of the proteins have been known for over a decade and are reported in Baumann et al., J. Bacteriol. 170:2045–2050 (1988). The 51.4 kD protein functions as the binding domain and the 41.9 kD protein functions as the toxin domain, thus, equimolar quantities of both proteins should usually be present for toxin function. Conveniently, this can be accomplished by having the nucleic acid sequence encoding both proteins downstream of the promoter-STAB-SD construct of the invention so that both proteins are present at the same time and in approximately the same amounts. If the nucleic acid sequence of only one of the two Bs toxin proteins is placed under the control of a promoter-STAB-SD sequence of the invention, it is desirable that a sequence encoding the other Bs toxin protein be placed under the transcriptional control of a like promoter construct so that the two proteins are produced in equimolar or roughly equimolar amounts.

In a surprising development, we have found that the Cyt1A protein from Bt can restore toxicity of the toxin to larvae which have lost receptors for the binding protein of the Bs binary toxin. Accordingly, if desired, the Cyt1A protein can be co-expressed in a cell expressing the 41.9 kD toxin protein of the Bs binary toxin in place of some or all of the 51.4 kD binding domain protein and the proteins will be toxic to target larvae ingesting the cell or biopesticides made from the cell. Thus, for example, a Bt cell, such as Bti, can be transformed by introducing a nucleic acid sequence encoding the Cyt1A protein with a promoter that will express amounts roughly similar to the amount of Bs 41.9 kD protein. Because the mechanism of action may not be the same as that of the 51.4 kD binding domain protein, it appears that the amount of the Cyt1A protein need not be as closely matched to the amount of the toxin protein as would be true for the 51.4 kD Bs binding protein to achieve full toxic effect.

IV. Bt Promoters

The invention uses promoters from Bt cry or cyt genes to drive the expression of Bs toxin. These genes encode the various insecticidal proteins produced by Bt. As noted in the previous section, Table I of Crickmore et al., Microbiol Mol Biol Rev., 62:807–813 (1998) sets forth a convenient listing of the names and GenBank accession numbers for the sequences of 120 Bt cry genes and 9 Bt cyt genes. Persons of skill in the art will appreciate that the 5' sequence preceding the start codon for the coding region described in the listing for each of these genes comprises the promoter region.

As persons of skill are aware, gene transcription of Cry and Cyt proteins is temporally regulated by the presence of sequences to which proteins known as sigma factors bind. The sigma factors recruit other proteins which form a complex permitting the RNA polymerase to initiate transcription of the DNA. The promoters of the cry or cyt genes are generally classified into three categories, based on the sigma factors which bind to them. They are the sigma-E promoters, the sigma-K promoters, and the sigma-A promoters.

The sigma-E promoters are also known as BtI promoters and sigma-K promoters are also known as BtII promoters (the terms "sigma-E" and "BtI" are used interchangeably herein, similarly, the terms "sigma-K" and "BtII" are used interchangeably). A number of cry genes are active during sporulation and are generally driven by BtI or BtII promoters, with BtI promoters active earlier in sporulation than are the BtII promoters. See generally, Agaisse and Lereclus, J. Bacteriol. 177:6027–6032 (1995) ("Agaisse and Lereclus 1995"). The sigma factors which recognize most cry genes are known. E.g., Agaisse and Lereclus 1995. For example, cry4A and B are recognized by BtI promoters.

A number of cry genes have two promoters, one BtI and one BtII. The combination of these dual promoters serves to extend the expression of the gene over a longer period of the sporulation process. In some cases, the two promoters overlap. Non-sporulation dependent cry genes have yet another set of promoters, which are recognized by yet another sigma factor, sigma-A. See, e.g., Agaisse and Lereclus 1995.

Any strong BtI or BtII promoter can be used in the nucleic acid sequences and methods of the invention. Dual BtI and BtII promoters, and particularly the overlapping BtI and BtII promoters, tend to be strong promoters of protein expression and are preferred forms of promoters for constructing nucleic acids of the invention. Members of the genes falling within the following groups which have dual promoters are especially preferred: cry1A, cry1B, cry11A, and cyt1Aa.

For purposes of the invention, any promoter which can drive expression of Cyt1Aa1 protein to comprise 15% or more of the dry weight of an acrystalliferrous Bti cell is considered a strong promoter. Any BtI or BtII promoter or promoter region which comprises both a BtI and BtII promoter and resulting in the protein constituting 15% or more of the dry weight of the cell constitutes an appropriate BtI or BtII promoter for purposes of the invention.

In preferred embodiments, the BtI or BtII promoter is a cry1 promoter or a cyt1Aa1 (also known as a cyt1A) promoter. Due to the close phylogenetic relationship and high sequence identity of the cry1 promoters (see, Crickmore et al., Microbiol. Mol. Biol. Rev. 62:807–813 (1998), any of the promoters of the genes designated in Crickmore et al. as a cry1 gene is considered capable of driving high levels of expression of Bs binary toxin. Particularly preferred embodiments are cry1Aa1 (formerly called cry1A (a)), cry1Ba1 (formerly called cry1B), cry1Ca1 (formerly called cry1C), and cry1Fa1 (formerly called cry1F). It should be noted that each of these genes has other closely related genes. For example, cry1Fa1 is closely related to cry1Fa2. The other members of the named cry1 gene groups designated by the same capital letter and same lower case letter are considered to be almost as preferred as the first listed gene in the group (that is, cry1Fa2 is almost as preferred as cry1Fa1).

In another particularly preferred embodiment, the promoter can be the promoter from cyt1Aa1, which comprises both BtI and BtII promoters, and is accordingly sometimes referred to as a dual promoter. Since the promoter region contains two promoters, the promoter region of this gene is also termed the "cyt1A promoters." Based on phylogenetic analysis and sequence identity, the promoters of the other cyt1Aa genes are also sufficiently strong BtI or BtII or combined BtI and BtII promoters to be used in the compositions and methods of the invention.

The non-sporulation dependent cry gene promoters are sigma-A promoters and are not generally satisfactory, except under a modified set of conditions. Non-sporulating forms of Bt, or course, do not divert their metabolic resources to spore production, and can accumulate toxin over a longer period than can sporulating forms. In non-sporulating forms, therefore, sigma-A promoters can be used to accumulate high levels of toxin. Accordingly, BtI and BtII promoters are preferred for use in Bacillus, including Bt and Bs. In non-sporulating forms of Bacillus, sigma-A promoters may be used.

V. STAB-SD Sequences

The crystal protein mRNAs of *B. thuringiensis* have an average half life of 10 minutes during sporulation, whereas the average half life of other mRNAs is between 1 to 2 minutes. This long half life may be responsible in part for the very high production of crystal proteins, which can be as much as 20–30% of the dry weight of the sporulated cells.

The long half life of these proteins is related to two untranslated regions of the genes. First, there is a sequence in the 5' untranslated region, usually found between the promoter and the coding region, which is not involved in translation initiation but which is a determinant of stability for mRNA. The sequence is a consensus Shine-Dalgarno-("SD") like sequence. Second, the 3' terminal fragment of cry genes, such as cry1Aa, increases the half life of mRNA transcripts two to threefold. Agaisse and Lereclus, Mol. Microbiol., 20:633–643 (1996) (hereafter "Agaisse 1996").

The 5' SD-like sequence appears to be involved in stabilizing the production of the proteins. It has, accordingly, been named a "STAB-SD" sequence. Agaisse 1996. Agaisse 1996 suggests that the STAB-SD is involved in interactions with the 3' end of 16S ribosomal RNA, and found that mutations of the STAB-SD sequence which were expected to abolish complementarity affected the stability conferred. Interestingly, the STAB-SD sequence of the protein then called cryIIIA (now called cry3A) showed putative interactions with the 3' end of *B. subtilis* 16S rRNA. Thus, it appears that STAB-SD sequences are not specific for particular species of bacteria, and that the STAB-SD sequences of other Bacillus species, and of other genera of bacteria, can be used to stabilize the production of proteins in *B. thuringiensis* and *B. sphaericus*.

Agaisse 1996 reviewed databases and identified numerous examples of putative STAB-SD sequences in 5' untranslated regions ("UTR"), including those of four cry genes from Bt, the cwp locus of *B. brevis*, and the inIAB locus of *Listeria monocytogenes*. Any of these STAB-SD sequences can be used to produce high levels of Bs toxin in Bacillus when placed between a strong Bacillus promoter and a ribosome binding site. The STAB-SD sequences identified share fairly high homology to one another.

In preferred embodiments, the STAB-SD sequence is selected from the group consisting of GAAAGGAGG (the cry3A sequence, SEQ ID NO:1), GAAGGGGGG (the cry3B sequence, SEQ ID NO:2), GAGGGGGGG (the cry3B2 sequence, SEQ ID NO:3), GAAAGGGGG (the cry3D sequence, SEQ ID NO:4), GAAAGGAGG (the cwp from *B. brevis* sequence, SEQ ID NO:5), and GAAAGGGGT (the inJAB from *L. monocytogenes*, SEQ ID NO:6). The cry3A, cry3B, cry3B2 and cry3D sequences are particularly preferred. Cry3A is the most preferred embodiment.

Other sequences with high sequence identity to one of the STAB-SD sequences set forth above and which function as a STAB-SD sequence can be used in the nucleic acids and methods of the invention. The sequence should have at least 85% sequence identity to the STAB-SD sequences set forth above. In preferred forms, the sequence has at least about 90% sequence identity, and even more preferably has about 95% or higher sequence identity. In addition, Agaisse 1996 provides guidance on changes to putative STAB-SD sequences which may deleteriously affect stability. In general, any change in a nucleotide which would abolish interaction between the STAB-SD sequence and the 3' end of *B. subtilis* 16SrRNA 3' is likely to reduce protein production and is not preferred.

Any putative nucleic acid sequence, or any desired modification to a known STAB-SD sequence, can be conveniently tested for its function as a STAB-SD protein by placing the sequence in a plasmid containing a galactosidase coding sequence following the assays and other methods taught in Agaisse 1996, or by substituting the sequence under consideration for the STAB-SD sequence in the procedure set forth in the Examples, below, and comparing the resulting protein production to the production of the same protein from the construct using the STAB-SD sequence set forth herein. Sequences which reduce production of Bs binary toxin to less than about 8 times that of wild-type Bs cells as measured by densiometric analysis of Coomassie blue-stained SDS-PAGE gels are less preferred.

VI. Assembly of Nucleic Acid Sequences of the Invention

Considerable information has developed in the art about the construction of promoters; in this context, the following discussion is offered to provide the specific information persons of skill may need to optimize placing a STAB-SD sequence between the sigma-factor binding site of a strong Bt promoter and the ribosome binding site.

FIG. 1 demonstrates an exemplary assembly of a nucleic acid sequence of the invention. In this embodiment, the cyt1A promoters comprise nucleotides 1–537. (Since the cyt1A gene contains two promoters, one a BtI promoter and the other a BtII promoter, the promoter region of the gene is sometimes referred to in the art as the "cyt1A promoters.") The binding sites for the sigma E-like factor and the sigma K-like factor are shown with the notations "SIGMA E" and "SIGMA K," respectively, placed over the appropriate regions, with the terms "–35" and "–10" and underlined sequences designating the specific binding sites. The underlined nucleotides with the letters "RBS" at nucleotides 726 to 730 and 2246 to 2249 denote ribosome binding sites.

The underlined nucleotides from 538 to 659 denote a sequence cloned in from the cry3A promoter. This sequence was cloned in to introduce the 9 nucleotide STAB-SD sequence; the longer sequence from the cry3A promoter was used because it is relatively more difficult to clone in a 9 nucleotide sequence. The sequence commencing at position 660 is a portion of the sequence of the binary toxin upstream of the coding region, followed by the coding region (as published by Baumann et al., J. Bacteriol. 170:2045–2050 (1988)). The particular portion upstream of the start codon at the position marked "+1" was selected simply because of the presence of a convenient restriction site. Shorter or longer portions could be used, and indeed, the entire promoter region of the binary toxin gene can be used if desired. In general, however, use of shorter sequences is preferred, not only for ease of manipulation but also to avoid the accidental inclusion of repressor sequences or the like which might happen to be present. Additionally, if a different sequence is used after the STAB-SD sequence, a ribosome binding site should be placed between the STAB-SD sequence and the start codon. Preferably, the ribosome binding site is positioned about 6 to about 10 nucleotides upstream of the start codon.

The start and stop sites of the 51.4 kD and 41.9 kD Bs binary toxin proteins are also shown.

The manner in which the elements of this exemplary sequence are joined can be varied substantially and still result in a sequence which works well in producing high levels of Bs binary toxin. In this sequence, some 121 nucleotides from the cry3A sequence were used to clone in the STAB-SD sequence. This was done simply for ease in cloning; the 9-nucleotide STAB-SD sequence can be introduced by itself. For ease in cloning, however, it is usually preferable to use a sequence which encompasses the STAB-SD sequence and which is from about 20 to about 130 nucleotides in length. The STAB-SD sequence itself can be placed anywhere from about 10 bases downstream of the sigma factor binding site to just before an RBS sequence, which in turn should be about 6 to about 10 bases upstream of the start codon. That is, all or a portion of the promoter downstream of the sigma-factor binding site can be deleted, with the understanding that if the RBS of the promoter is deleted, another RBS, such as that from the Bs binary toxin, should be placed about 6 to about 10 bases upstream of the start codon. As noted, in the sequence depicted in FIG. 1, the sequence from position 660 on are from the native Bs binary toxin gene. Any particular sequence can be readily tested by substituting it in the assays taught in the Examples to determine whether it has a deleterious or advantageous effect on toxin production.

VII. 20 kD Chaperone-like Protein

In the methods of the present invention, host cells are transformed with a gene encoding a 20 kDa protein gene, which encodes a known protein (Frutos et al., supra; Visick & Whitely, supra), to enhance the production of Bs binary toxin. The 20 kDa protein gene can be isolated and sequenced, for example, from two subspecies of *B. thuringiensis* (nitos et al., *Biochem. Syst. and Ecol.* 19: 599–609 (1991)). The level of expression of the 20 kDa protein has been characterized in cells transformed with the 20 kDa protein gene. Using methods and sequence information described herein and in International Patent Application WO 97/39623, the 20 kDa protein gene can be isolated by those skilled in the art and used to construct recombinant expression vectors for transformation of a host cell.

The host cells transformed with the 20 kD protein gene should be competent to express Bs binary toxin. The cells may express the Bs binary toxin, or the cells may be transformed with exogenous binary toxin expression vectors. As noted earlier, the sequence of both proteins of the Bs binary toxin is known. This sequence information can be used by one skilled in the art, along with the methods described herein, to construct recombinant vectors for transformation of a host cell, such as a Bs cell, with the gene encoding the 20 kD protein. Conveniently, the gene for the 20 kD protein can be placed on the same plasmid as the nucleic acid sequence for expressing high levels of Bs toxin.

VIII. Nucleic Acids Sequences and Vectors

A recombinant expression vector for transformation of a host cell is prepared by first isolating the constituent polynucleotide sequences, as discussed herein. The polynucleotide sequences, e.g., a sequence encoding the Bs binary toxin driven by a promoter as discussed above, are then ligated to create a recombinant expression vector suitable for transformation of a host cell. Methods for isolating and preparing recombinant polynucleotides are well known to those skilled in the art. Sambrook et al., *Molecular Cloning. A Laboratory Manual* (2d ed. 1989); Ausubel et al., *Current Protocols in Molecular Biology* (1995)), provide information sufficient to direct persons of skill through many cloning exercises.

One preferred method for obtaining specific polynucleotides combines the use of synthetic oligonucleotide primers with polymerase extension or ligation on a mRNA or DNA template. Such a method, e.g., RT, PCR, or LCR, amplifies the desired nucleotide sequence (see U.S. Pat. Nos. 4,683, 195 and 4,683,202). Restriction endonuclease sites can be incorporated into the primers. Amplified polynucleotides are purified and ligated to form an expression cassette. Alterations in the natural gene sequence can be introduced by techniques such as in vitro mutagenesis and PCR using primers that have been designed to incorporate appropriate mutations. Another preferred method of isolating polynucleotide sequences uses known restriction endonuclease sites to isolate nucleic acid fragments from plasmids. The genes of interest can also be isolated by one of skill in the art using primers based on the known gene sequence.

The isolated polynucleotide sequence of choice, e.g., the Bs binary toxin driven by the promoter sequence discussed above, is inserted into an "expression vector," "cloning vector," or "vector," terms which usually refer to plasmids or other nucleic acid molecules that are able to replicate in a chosen host cell. Expression vectors can replicate autonomously, or they can replicate by being inserted into the genome of the host cell. Often, it is desirable for a vector to be usable in more than one host cell, e.g., in *E. coli* for cloning and construction, and in *B. thuringiensis* for expression. Additional elements of the vector can include, for example, selectable markers, e.g., tetracycline resistance or hygromycin resistance, which permit detection and/or selection of those cells transformed with the desired polynucleotide sequences (see, e.g., U.S. Pat. No. 4,704,362). The particular vector used to transport the genetic information into the cell is also not particularly critical. Any suitable vector used for expression of recombinant proteins host cells can be used. A preferred vector is pHT3101, which is an *E. coli-B. thuringiensis* shuttle vector (Lereclus et al., *FEMS Microbiol. Lett.* 60: 211–218 (1989)).

Expression vectors typically have an expression cassette that contains all the elements required for the expression of the polynucleotide of choice in a host cell. A typical expression cassette contains a promoter operably linked to the polynucleotide sequence of choice. The promoter used to direct expression of the Bs binary toxin is as described above, and is operably linked to a sequence encoding one or both of the Bs binary toxin proteins. The promoter is preferably positioned about the same distance from the heterologous transcription start site as it is from the transcription start site in its natural setting. As is known in the art, however, some variation in this distance can be accommodated without loss of promoter function. For expression of the 20 kD protein encoded by the cry11A operon, other promoters suitable for driving the expression of a heterologous gene in a host cell can be used, including those typically used in standard expression cassettes, e.g., the β-galactosidase promoter. In one embodiment of the invention, the 20 kD protein gene is operably linked to the BtI and BtII promoters ("the cry1Ac promoter") of the cry1Ac gene, creating a heterologous nucleic acid operably linked to a promoter. The cry1Ac promoter is highly active in growth conditions that induce sporulation.

IX. Expression of Protein

After construction and isolation of the recombinant expression vector, it is used to transform a host cell for expression of Bs binary toxin. The particular procedure used to introduce the genetic material into the host cell for expression of a protein is not particularly critical. Any of the well known procedures for introducing foreign polynucleotide sequences into host cells can be used. Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods (see generally Sambrook et al., supra; Ausubel et al., supra). In some embodiments, the host cells can be transformed by homologous recombination, as described in Poncet et al., *Appl Environ Microbiol.* 63:4413–4420 (1997). A preferred method of transforming *B. thuringiensis* is electroporation, as described in Wu et al., *Mol. Microbiol.* 13: 965–972 (1994).

Hosts for transformation with the Bs binary toxin gene include any suitable host bacterial cell competent to express the protein, especially members of the genus Bacillus. In particularly preferred embodiments, the cells are Bs or Bt cells. Hosts that are transformed with the Bs binary toxin are useful recombinant bacteria as insecticides. Preferred subspecies of *B. thuringiensis* include, e.g., *B. thuringiensis* subsp. *kurstaki, B. thuringiensis* subsp. *aizawai, B. thuringiensis* subsp. *israelensis*, and *B. thuringiensis* subsp. *tenebrionis*. A preferred strain is Bti IPS82.

After the host cell is transformed with the Bs binary toxin gene, the host cell is incubated under conditions suitable for expression of the toxin. Typically, the host will be grown under conditions that promote sporulation and expression of insecticidal endotoxin genes. Host cells may be prepared in any quantity required by fermenting an inoculum in standard media known to those skilled in the art. The media will, for example, generally contain a nitrogen source and a carbohydrate source, e.g., glucose. Suitable conditions for incubation include a temperature in the range of 15–45° C., preferably 30° C., and an approximately neutral pH. Incubation may be conveniently carried out in batches, typically for a period of 3–5 days.

Various media for growing Bt and Bs cells are known in the art. In some preferred embodiments, an inoculum from a stock host cell culture is grown on nutrient agar (BBL Microbiology Systems) or peptonized milk (1% peptonized milk [BBL Microbiology Systems], 1% dextrose, 0.2% yeast extract, 1.216 mM $MgSO_4$, 0.072 mM $FeSO_4$, 0.139 mM $ZnSO_4$, 0.118 mM $MnSO_4$) with erythromycin at a concentration of 25 μg/ml, as described in the Examples.

Enhanced production of Bs binary toxin is observed after host cells competent to express the Bs binary toxin gene is transformed with the gene and the cells are grown under suitable conditions. Enhanced production of Bs binary toxin may be observed by standard methods known to those skilled in the art. For example, parasporal inclusions of insecticidal endotoxins can be purified (see Wu & Federici, *Appl. Microbiol. Biotechnol.* 42: 697–702 (1995) (hereafter "Wu and Federici 1995"), harvested by centrifugation from lysed cultures, or examined with microscopy (see Wu & Federici 1995, supra). Parasporal inclusions that have been harvested by centrifugation or purified may be separated using standard methods known in the art, for example, chromatography, immunoprecipitation, ELISA, bioassay, western analysis, or gel electrophoresis (see, e.g., Wu & Federici 1995, supra; Ausubel, supra). Amounts of protein are quantified by suitable means, including width and intensity of stained bands, densitometry, bioactivity, and fluorescence. For transformed Bt cells or other cells known not to synthesize Bs binary toxin in their untransformed state, all production of Bs binary toxin is considered to represent enhancement by the methods of the invention. Where Bs cells are transformed with the nucleic acids of the invention, the net amount of toxin produced by the transformed cells can be compared to like untransformed cells. Net amount of toxin refers to the amount of Bs binary toxin in parasporal bodies or crystals. The control hosts are otherwise genetically identical with the transformed hosts and grown on comparative media. Enhancement is any statistically significant increase in Bs binary toxin production. In a preferred embodiment, parasporal bodies are isolated by centrifugation from lysed cultures and are examined by SDS-PAGE gels stained with Coomassie blue.

EXAMPLES

Example 1

Expression Levels of Bs Binary Toxin Produced in Bti Using a Bti Promoter, STAB-SD Sequence, and Coding Sequence for the Toxin

A *Bacillus sphaericus* 2362 binary toxin gene was introduced into an acrystalliferous strain (4Q7) of *Bacillus thuringiensis* subsp. *israelensis* (Bti) using cyt1A promoters and a STAB-SD sequence placed into the plasmid pHT3101. The construct resulted in binary toxin production which appears to be 15-fold or more greater per unit of culture medium than that obtained with the parental (wild type) *B. sphaericus* strain grown on the same medium, as assessed by densiometric scanning of gels produced by sodium dodecyl sulfate-polyacrylamide gel electrophoresis (SDS-PAGE).

TABLE 1

Yield Increases Obtained Using cyt1A Promoters and the STAB-SD Sequence to Drive Expression of the Bs 2362 Binary Toxin Gene Operon

| Strain | Increase in Binary Toxin | Decrease in Bti Toxins |
|---|---|---|
| Bs 2362 (wild type) | 1 | — |
| Bti IPS82 (Wild type) | — | 1 |
| Bti4Q7/Bs Binary toxin | >15 x | — |
| Bti IPS82 + Bs Binary toxin | >20 x | .15–.35 |

Example 2

Toxicity of Non-toxic Bti Engineered to Express Bs Binary Toxin

The toxicity of the acrystalliferous 4Q7 Bti strain, transformed to produce Bs 2362 binary toxin, was tested on fourth instar larvae ("$L_4$") of *Culex quinquefasciatus* and compared to the wild type Bs 2362 strain grown on the same medium. (Bti strain 4Q7 does not normally produce Bs or Bti toxins.) $LC_{50}$ is the amount of toxin required to kill 50% of the larvae present in a sample during a test.

As shown on Table 2, below, the amount of wild-type Bs 2362 needed to kill 50% ("$LC_{50}$") of fourth instar larvae of Culex mosquitoes was 15.0 ng/ml. The 4Q7 Bti strain, transformed by nucleic acids of the invention to express Bs toxin, had an LC50 of 1.4, or approximately 10 times better toxicity than that of unaltered Bs.

Example 3

Toxicity of Bti Engineered to Express Bs Binary Toxin

Transformation of *Bacillus thuringiensis* subsp. *israelensis* with the plasmid described in Example 1 that produces the Bs 2362 binary toxin increased toxicity by at least 10-fold against Culex species compared to either of the parental strains (Bs or Bti).

Bti IPS82 is the strain of Bti used as a commercial biopesticide. As can be seen from Table 2, the amount of this strain needed to kill 50% ("$LC_{50}$") of fourth instar lavae ("$L_4$") of Culex mosquitoes was 19.5 ng/ml. Wild-type Bs strain 2362 had an LC50 of 15 ng/ml. The Bti IPS82 strain, transformed by nucleic acids of the invention to express Bs toxin, had an LC50 of 1.5, or approximately 13 times better toxicity than that of unaltered Bs.

TABLE 2

Toxicity of a Bti/Bs2362 Recombinant to $L_4$ *Culex quinquefasciatus*

| Strain | $LC_{50}$ (ng/ml) | Ratio Bti Bti/Bs | Ratio Bs Bti/Bs |
|---|---|---|---|
| Bti IPS82 | 19.5 | 1.0 | — |
| Bs 2362 | 15.0 | — | 1.0 |
| Bti4Q7/Bs Binary toxin | 1.4 | — | 10.0 |
| Bti IPS82 + Bs Binary toxin | 1.5 | 13.0 | — |

Example 4

Materials and Methods Used in Examples 1–3

A. Bacterial Strains, Gene, Plasmids and Transformation

*Bacillus sphaericus* strain 2362 was obtained from a powdered preparation that was kindly provided by Abbott Laboratories (North Chicago, Ill.). *Escherichia coli-B. thuringiensis* shuttle expression vector pHT3103 (Lereclus et al. FEMS Microbiol. Lett. 51:211–7 (1989)) was used to make and amplify the plasmid construct (pPHSP-1) in *E. coli* DH5α. The pPHSP1 construct was expressed in an acrystalliferous strain, 4Q7, of *B. thuringiensis* subsp. *israelensis* obtained from the Bacillus Stock Center at Ohio State University (Columbus, Ohio), or in *B. thuringiensis* subsp. *israelensis* IPS82 (Abbott Laboratories). The modified pHT3101-based vector (pSTAB-SD) containing the 660-bp fragment with the cyt1A promoters and STAB-SD sequence (Agaisse and Lereclus, Mol. Microbiol., 20:633–643 (1996)) was previously described (Park et al., FEMS Microbiol Lett 181:319–327 (1999)). Plasmids were purified using the QIAprep Spin Miniprep Kit (Qiagen Inc.). Bacillus strains were transformed by electroporation as described by Park et al. App Environ. Microbiol 64:3932–3938 (1998).

B. PCR amplification of the Gene Encoding the *B. sphaericus* Entomocidal Proteins A crude plasmid preparation was made from *B. sphaericus* 2362 using the alkaline lysis method (Sambrook et al., 1989). The gene encoding the 54.1 kDa protein and 41.9 kDA entomocidal protein of *B. sphaericus* (Baumann et al., J. Bacteriol. 170:2045–2050 (1988), GenBank M20390) was obtained by PCR using Vent (Exo+) DNA polymerase (Biolabs) and the primers BSP-1 (5' aactgcaCTTGTCAACATGTGAAGATTAAAGGTAACTT TCAG-3'; SEQ ID NO:10) and BSP-2 (5'-aactcag CCAAA-CAACAACAGTTTACATTCGAGTGTAAAA GTTC-3'; SEQ ID NO:11) (Genosys). The 3.4 kbp PCR product was digested with PstI and cloned in the same site in pHT3101 to generate pHBS. The 3.0 kbp HpaI-PstI fragment in pHBS was cloned into the filled XbaI and PstI sites in pSTAB-SD to generate pPHSP-1.

C. Growth of Bacterial Strains

The strains *B. thuringiensis* subsp. *israelensis* 4Q7/pPHSP-1 and *B. thuringiensis* subsp. *israelensis* IPS82/pPHSP-1 were grown on nutrient agar (BBL Microbiology Systems) or peptonized milk (1% peptonized milk [BBL Microbiology Systems], 1% dextrose, 0.2% yeast extract, 1.216 mM $MgSO_4$, 0.072 mM $FeSO_4$, 0.139 mM $ZnSO_4$, 0.118 mM $MnSO_4$) with erythromycin at a concentration of 25 μg/ml. For insect bioassays, *B. thuringiensis* subsp. *israelensis* IPS82/pPHSP1 was grown in 25 ml of peptonized milk with erythromycin (25 μg/ml) in a shaker incubator set at 28° C., 250 rpm/min for 6 days, during which time >98% of the cells had sporulated and lysed. Spores and crystals were harvested by centrifugation at 4° C., 6,000×g for 15 min. The pellet was washed twice in water and dried in a vacuum chamber.

D. Sodium Dodecyl Sulfate-polyacrylamide Gel Electrophoresis (SDS-PAGE)

After 6 days growth in peptonized milk, 1 ml of the lysed culture was collected and centrifuged at 10,000×g for 5 min. The medium was discarded and 150 μl of TE buffer (10 mM Tris-Cl, pH 7.5, 1 mM EDTA) and 150 of 2×sample buffer (Laemmli, 1970) was added. Proteins were fractionated by SDS-PAGE (Laemmli, 1970).

E. Bioassays

For bioassays, groups of 20 early fourth instars were exposed to a range of concentrations of the lyophilized spore/crystal powders in 100 ml of deionized water held in 237 ml plastic cups. Seven to 9 different concentrations of the powders were replicated on 5 different days.

F. Microscopy

Sporulating cultures were monitored by light microscopy with a Zeiss Photomicroscope III, using a 100×oil immersion objective. For transmission electron microscopy, sporulated cells from peptonized milk cultures were collected just before lysis, fixed for 2 hr in 3% phosphate-buffered glutaraldehyde and 0.25% sucrose, post-fixed in 1% $OsO_4$, dehydrated in ethanol-propylene oxide, and embedded in Epon-Araldite (Ibarra and Federici, J. Bacteriol. 165:527–533 (1986)). Ultrathin sections of sporulated cells were examined and photographed in a Hitachi 600 electron microscope operating at an accelerating voltage of 75 kV.

Example 5

Cyt1A Protein Restores Susceptibility to Bs Toxin to Mosquitoes Highly Resistant to That Toxin A. Materials and Methods Bacterial Strains and Toxins.

Toxin preparations used in this study were lyophilized powders of lysed cultures of *B. sphaericus* 2362 and a recombinant strain of *B. thuringiensis* subsp. *israelensis* that only produces Cyt1Aa (Wu and Federici, J. Bacteriol. 175:5276–5280 (1993)). These powders contained the spore and the crystal (that is, the parasporal body) along with cell debris and media solids resulting from lyophilization. The specific powders tested were (1) *B. sphaericus* strain 2362, obtained as a technical powder of the wild-type strain from Abbott Laboratories (North Chicago, Ill.); (2) Cyt1Aa, a recombinant strain of *BTI* noted above; and (3) *BTI* 4Q7, an acrystalliferous strain of this subspecies that does not produce any endotoxins. This strain was obtained from the Bacillus Stock Center (Ohio State University, Columbus, Ohio) and used as one of the controls. Lyophilized powders of purified Cyt1A crystals (Wu and Federici, supra) were also used.

Toxin Powder Production and Storage.

Bacterial strains producing the various toxins were grown on solid or liquid media as described previously (Wirth et al., Proc Natl. Acad. Sci USA, 94:10536–10540 (1997), Park et al., Appl Environ Microbiol. 64:3932–3938 (1998)). The sporulated cells were washed in distilled water, sedimented, and the resultant pellet was lyophilized. For mosquito selections and bioassays, stock suspensions of the powders were prepared in distilled water and homogenized with the aid of approximately 25 glass beads. Stocks were prepared monthly and ten-fold serial dilutions were prepared weekly. All stocks and dilutions were frozen at −20° C. when not in use.

Mosquito Strains.

Two strains of *Cx. quinquefasciatus* were used; *BS*-R, a strain resistant to *B. sphaericus* 2362, and Syn-P, an unselected, non-resistant strain. *BS*-R has been selected with *B. sphaericus* 2362 since 1992 and routinely survives 48 h of exposure to 1000 μg/ml, a concentration 149,000-fold higher than the concentration which kills 50% of Syn-P, the sensitive reference strain. Syn-P is a "synthetic" population of *Cx. quinquefasciatus* derived from larval populations collected in 1995 from 3 different geographic areas in southern California. This colony has been maintained in the laboratory without exposure to *B. sphaericus*.

Selection and Bioassay Procedures.

As noted above, the *BS*-R strain has been maintained under selection pressure with *B. sphaericus* 2362 since 1992. Selection consisted of exposing groups of ca. 1,000 early fourth-instars to concentrations of *B. sphaericus* ranging between 100–120 μg/ml in enameled metal pans in about 1 L of deionized water for 48–96 h. Average mortality of the larvae under selection was 10% or less per selection, and the survivors were used to continue the colony.

For bioassays, groups of 20 early fourth instars were exposed to a range of concentrations of the lyophilized spore/crystal powders in 100 ml of deionized water held in 237 ml plastic cups. Seven to 9 different concentrations of the powders, which yielded mortality between 2 and 98% after 48 h, were replicated on 5 different days. For the bioassays in which different combinations of Cyt1A and *B. sphaericus* 2362 were tested, different ratios of these toxins were based on the weights of the lyophilized powders of the bacterial strain.

Because the quantity of purified Cyt1A crystals was limited, bioassays with this powder utilized 10 early fourth instars held in 10 ml of deionized water in 30 ml plastic cups and replicated on 2–3 different days. Bioassays combining *B. sphaericus* 2362 technical powder and Cyt1A purified crystals at a 10:1 ratio (10 parts *B. sphaericus* 2362:1 part Cyt1A crystal) were based on the weights of the lyophilized powders of *B. sphaericus* 2362 and Cyt1A.

All data were subjected to probit analysis using a program for the PC. Dose-response values with overlapping fiducial limits were not considered to be significantly different. Resistance ratios were calculated by dividing the respective lethal concentration value for the *BS*-R strain by that of the Syn-P strain. Resistance ratios whose fiducial limits contained the number 1 were not considered to be significant.

Evaluation of Synergism.

Synergistic interactions between *B. sphaericus* 2362 and Cyt1A were evaluated using the method of Tabashnik, Appl Environ Entomol 58:3343–3346 (1992). Theoretical lethal concentration values for the different mixtures of Cyt1A and *B. sphaericus* 2362 were calculated from the weighted harmonic means of the individual values for these toxins. Because the *B. sphaericus* 2362 powder was not toxic to the *BS*-R strain at any of the concentrations tested, the calculation of the theoretical toxicity of a combination of Cyt1A and *B. sphaericus* 2362 was based on the toxicity and proportion of Cyt1A alone for this strain. The synergism factor (SF), defined as the ratio of the theoretical lethal concentration value to the observed lethal concentration value, was determined for combinations of *B. sphaericus* 2362 and the Cyt1A strain as well as for combinations of *B. sphaericus* 2362 and purified Cyt1A crystals. When the ratio was greater than 1, the toxin interaction was considered synergistic because toxicity exceeded the value predicted from individual additive toxicity. When the ratio was less than 1, the interaction was considered antagonistic, whereas a ratio of 1 indicated that the values were additive.

B. Results

In the bioassays to determine toxin baseline values under standard conditions against the resistant and sensitive mosquito strains, no mortality resulted from exposure of BS-R, the resistant strain of Cx. quinquefasciatus, to 1000 μg/ml of B. sphaericus 2362. This concentration was 149,000 fold higher than the $LC_{50}$ (0.0067 μg/ml) obtained against Syn-P, the sensitive strain. When the bioassays were carried out in 10 ml of water with 10 larvae per cup rather than 20 larvae in 100 ml, no mortality was obtained against BS-R, but the toxicity of BS 2362 was lower ($LC_{50}$, 0.032 μg/ml) against Syn-P. Increasing larval density has been previously shown to require lower amounts of Bti toxin to induce the same level of mortality observed at lower densities (Aly et al. 1988). The estimated difference in the sensitivity of BS-R and Syn-P using the smaller bioassay system was 31,000 fold.

The Cyt1A bacterial strain was slightly less toxic to the BS-R strain ($LC_{50}$, 32.5 μg/ml) than to Syn-P ($LC_{50}$, 11.7 μg/ml) in the standard bioassay system. However, in the tests using Cyt1A crystals in the smaller bioassay system, no difference in sensitivity ($LC_{50}$s, ca. 20 μg/ml) was observed between BS-R and Syn-P.

Adding Cyt1A to the B. sphaericus 2362 preparations restored most of its toxicity against the BS-R resistant Cx. quinquefasciatus strain. A B. sphaericus 2362 ratio to Cyt1A of 10:1 was highly toxic to both the resistant and sensitive mosquito strains. Toxicity levels for this combination were higher against Syn-P than BS-R, with $LC_{95}$ values of 0.442 and 36.6 μg /ml, respectively, and a resistance ratio ($LC_{95}$) of 82.9 for BS-R. The 5:1 ratio was more toxic toward Syn-P and BS-R, and the resistance ratio at the $LC_{95}$ level was reduced to 34.4-fold. At a ratio of 3:1 B. sphaericus 2362:Cyt1A, the mixture was again significantly more toxic to BS-R ($LC_{50}$, 1.99 μg/ml), and the resistance ratio decreased to 15.4 fold at the $LC_{95}$ level. Toxicity at a 1:1 ratio against BS-R was not significantly different from that of the 3:1 ratio. Overall, as the proportion of B. sphaericus 2362 to Cyt1A was increased, the toxicity increased toward both the resistant and sensitive mosquito strains. However, the resistance ratios at the $LC_{95}$ values for BS-R declined to insignificant levels for ratios of 1:3, 1:5, and 1:10, in which Cyt1A was the principal component.

Calculation of the SF for these combinations revealed significant synergism between Cyt1A and B. sphaericus 2362 against the BS-R strain, but not against Syn-P. SF values ranged from 10–137 at the $LC_{95}$ level for BS-R. The highest levels of synergism were observed in the combinations in which Cyt1A was present in the lowest proportion (10:1, 5:1, 3:1). These combinations were antagonistic toward Syn-P at the $LC_{95}$ level at ratios 1:10, 1:5, and 1:3, and additive or mildly synergistic at ratios of 1:1, 3:1, 5:1, and 10:1, i.e., where B. sphaericus became the predominant component.

Bioassays using B. sphaericus 2362 combined with the purified Cyt1A crystals at a ratio of 10:1 demonstrated that this combination was highly toxic to both BS-R ($LC_{95}$, 4.96 μg/ml) and Syn-P ($LC_{95}$, 2.37 μg/ml). Although the BS-R strain was slightly less sensitive to the mixture, the toxicity values were not significantly different. Importantly, no resistance was detected against the BS-R strain with this combination, which had a high SF value of 278.

C. Discussion

Combining Cyt1A with BS 2362 restored the toxicity of the latter against a highly resistant strain of Cx. quinquefasciatus. Moreover, we were able to completely restore toxicity with sublethal concentrations of Cyt1A crystals, and therefore suppress resistance to B. sphaericus in the BS-R mosquito strain. In contrast to the high level of activity observed against the resistant mosquito population, little or no enhanced activity resulted with these same mixtures against the non-resistant reference strain, Syn-P.

The ability of Cyt1A at low concentrations to restore high toxicity to B. sphaericus 2362 against resistant mosquitoes has practical implications for control of Culex populations and provides insight into its mode of action. Bacterial larvicides based on B. sphaericus are used in several countries and resistance in field populations of Cx. quinquefasciatus has already been reported in France, Brazil, and India. The results of our studies indicate that adding Cyt1A at a ratio as low as 1:10 to B. sphaericus larvicides restores most of the toxicity against even highly resistant populations of Cx. quinquefasciatus. Therefore, Cyt1A provides a practical tool for managing B. sphaericusresistance. Furthermore, adding a small quantity of Cyt1A to B. sphaericus preparations can delay resistance in mosquito populations in which it has not already developed.

Others have shown that a different Cyt protein, Cyt1Ab from B. thuringiensis subsp. medellin, can suppress resistance to B. sphaericus 2297, a mosquitocidal strain of this bacterium that produces a large toxin crystal, in Cx. pipiens (Thiéry et al. 1998). However, Cyt1Ab's suppression of resistance to B. sphaericus 2297 was much less effective than Cyt1A's suppression of resistance to B. sphaericus. The reduced capacity of Cyt1Ab to suppress resistance to B. sphaericus 2297 may be due to the 5-fold lower toxicity of this Cyt toxin to Cx. pipiens in comparison to Cyt1A (Thiéry et al. Appl Environ Microbiol 63:468–473 (1997)).

Just how Cyt1A restores the toxicity of B. sphaericus 2362 is unknown. However, previous studies of the mechanism of resistance in our BS-R strain of Cx. quinquefasciatus and Cyt1A's binding properties suggest that Cyt1A assists binding and insertion of the toxin into the microvillar membrane. Our resistant strain of Cx. quinquefasciatus has no functional receptor for the B. sphaericus 2362 toxin and therefore it cannot bind effectively to the midgut microvilli. Studies of Cyt1A have shown that it perturbs membranes by binding to the lipid portion, and that it also binds to Cry toxins. Moreover, in the presence of the BTI Cry toxins, Cyt1A binds to the microvilli of cells in the gastric caeca and posterior midgut of mosquito larvae. These observations suggest several mechanisms for restoring B. sphaericus toxicity. The Cyt1A and B. sphaericus toxins may bind together after dissolution, and then insert into the membrane as a complex due to Cyt1A's lipophilic properties. Another possibility is that Cyt1A may first bind to the membrane after which the B. sphaericus toxin binds to Cyt1A and inserts into the membrane. Finally, Cyt1A may permeate the membrane causing lesions that allow the B. sphaericus toxin to gain access to the original target.

The synergism we obtained with the combinations of Cyt1A and B. sphaericus 2362 also provides additional evidence that Cyt1A enhances toxicity by assisting other protein toxins in binding to the mosquito microvillar membrane, especially those that do not bind efficiently. In previous studies we demonstrated that Cyt1A can synergize Cry4 and Cry11 toxins from mosquitocidal strains of B. thuringiensis against resistant mosquitoes. However, synergism in non-resistant mosquitoes was observed only with the Cry4 and Cry11A toxins of BTI, not with the Cry11B toxin from B. thuringiensis subsp. jegathesan, which is much more toxic than Cry11A. A similar pattern of synergism was observed in the current study wherein Cyt1A synergized the toxicity of B. sphaericus 2362 against the resistant BS-R strain, but not against the sensitive Syn-P strain. The implication of these results, in conjunction with those obtained in the previous studies cited above, is that toxins which are highly toxic or have a high binding affinity, such as Cry11B or the B. sphaericus 2362 binary toxin, gain little or no value from assisted binding by Cyt1A. But when the toxin receptors are modified or lost through resistance, Cyt1A's ability to bind to and perturb the microvillar membrane restores the capacity of these toxins to insert into the membrane and exert toxicity. As both the Cyt1A and B. sphaericus toxins dissolve in the mosquito midgut lumen, they may associate immediately after dissolution in the lumen as well as at the microvillar membrane surface. An implication of these results is that Cyt1A, and possibly other Cyt proteins, may extend the insecticidal spectrum of non-Cyt protein toxins to other insect species.

TABLE 3

Toxicity of *B. sphaericus* (strain 2362) technical powder, CytlA crystal/spore powder from *B. t.* subsp. *israelensis*, and various combinations of *B. sphaericus* and CytlA against susceptible (Syn-P) and *B. sphaericus* resistant (BS-R) *C. quinquefasciatus*

| Toxin(s) | Strain | No. | $LC_{50}$ (μg/ml) (fiducial limits) | $LC_{95}$ (μg/ml) (fiducial limits) | Slope (± SE) | $\chi^2$ | Resistance ratio at $LC_{50}$ (FL) | Resistance ratio at $LC_{95}$ (FL) | SF $LC_{50}$ | SF $LC_{95}$ |
|---|---|---|---|---|---|---|---|---|---|---|
| *B. sphaericus* (strain 2362) | Syn-P | 1,100 | 0.00671 (0.0055–0.0082) | 0.466 (0.300–0.790) | 0.89 (0.045) | 13.1 | 1.0 | 1.0 | | |
| | BS-R | 600 | No mortality at 1,000 μg/ml | | | | ~149,000 | | | |
| CytlA | Syn-P | 600 | 11.7 (10.2–13.4) | 59.8 (47.7–79.7) | 2.3 (0.16) | 7.3 | 1.0 | 1.0 | | |
| | BS-R | 700 | 32.5 (28.3–37.6) | 222 (172–304) | 2.0 (0.12) | 4.1 | 2.7 (2.3–3.3) | 3.7 (2.6–5.3) | | |
| *B. sphaericus* + CytlA (10:1)[a] | Syn-P | 900 | 0.0288 (0.0163–0.0508) | 0.0422 (0.162–1.23) | 1.4 (0.21) | 22.8 | 1.0 | 1.0 | 0.26 | 1.2 |
| | BS-R | 800 | 2.47 (1.46–4.20) | 36.6 (14.0–97.4) | 1.4 (0.17) | 25.4 | 85.8 (56.8–129) | 82.9 (39–174) | 132 | 61 |
| *B. sphaericus* + CytlA (5:1) | Syn-P | 700 | 0.0274 (0.0232–0.0322) | 0.278 (0.209–0.397) | 1.6 (0.10) | 2.4 | 1.0 | 1.0 | 0.29 | 2.0 |
| | BS-R | 1,000 | 1.23 (1.05–1.43) | 9.58 (7.49–12.9) | 1.8 (0.11) | 12.5 | 45.0 (38.1–53.2) | 34.4 (25.2–46.9) | 155.9 | 136.8 |
| *B. sphaericus* + CytlA (3:1) | Syn-P | 800 | 0.0147 (0.0086–0.0354) | 0.652 (0.177–2.48) | 1.0 (0.12) | 27.1 | 1.0 | 1.0 | 0.6 | 1.0 |
| | BS-R | 600 | 1.99 (1.80–2.22) | 7.17 (5.87–9.31) | 2.9 (0.22) | 6.0 | 297 (255–347) | 15.4 (10.9–1.7) | 65 | 124 |
| *B. sphaericus* + CytlA (1:1) | Syn-P | 1,000 | 0.0381 (0.0323–0.0449) | 0.464 (0.348–0.655) | 1.5 (0.08) | 10.1 | 1.0 | 1.0 | 0.35 | 2.0 |
| | BS-R | 1,000 | 0.735 (0.632–0.853) | 6.49 (5.06–8.73) | 1.7 (0.09) | 5.8 | 19.3 (16.5–22.5) | 14.0 (10.5–18.7) | 88 | 69 |
| *B. sphaericus* + CytlA (1:3) | Syn-P | 900 | 0.234 (0.191–0.287) | 7.54 (5.00–12.5) | 1.1 (0.06) | 11.5 | 1.0 | 1.0 | 0.11 | 0.24 |
| | BS-R | 900 | 1.71 (1.45–2.00) | 18.4 (14.1–25.5) | 1.6 (0.09) | 6.5 | 7.3 (6.3–8.5) | 2.4 (1.8–3.2) | 25 | 16 |
| *B. sphaericus* + CytA (1:5) | Syn-P | 1,000 | 0.189 (0.149–0.236) | 6.74 (4.66–10.6) | 1.1 (0.06) | 13.5 | 1.0 | 1.0 | 0.21 | 0.39 |
| | BS-R | 900 | 1.56 (1.34–1.81) | 11.8 (9.23–15.9) | 1.9 (0.11) | 8.9 | 8.2 (6.9–9.6) | 1.8 (1.3–2.3) | 25.3 | 23.0 |
| *B. sphaericus* + CytlA (1:10) | Syn-P | 900 | 1.06 (0.859–1.29) | 25.9 (18.1–40.1) | 1.2 (0.07) | 4.8 | 1.0 | 1.0 | 0.10 | 0.17 |
| | BS-R | 900 | 4.72 (4.12–5.38) | 24.6 (19.8–32.0) | 2.3 (0.15) | 13.0 | 4.4 (3.7–5.2) | 1.0 (0.69–1.3) | 7.7 | 10.0 |

SF, synergism factor.
[a]Ratios in brackets represent the relative proportion of *B. sphaericus* technical powder to CtylA spore/crystal powder (BS:CytA). All ratios were based on the weight of each respective powder.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

SEQUENCE LISTING

<160> NUMBER OF SEQ ID NOS: 11

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence:STAB-SD from
      Bacillus thuringiensis cry3A gene

<400> SEQUENCE: 1 gaaaggagg                                                                9

```
<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence:STAB-SD from
      Bacillus thuringiensis cry3B gene

<400> SEQUENCE: 2 gaagggggg                                                                 9

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:STAB-SD from
      Bacillus thuringiensis cry3B2 gene

<400> SEQUENCE: 3 gagggggg                                                                  9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:STAB-SD from
      Bacillus thuringiensis cry3D gene

<400> SEQUENCE: 4 gaaaggggg                                                                 9

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence:STAB-SD from
      Bacillus brevis cwp gene

<400> SEQUENCE: 5 gaaaggagg                                                                 9

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence:STAB-SD from
      Listeria monocytogenes inIAB gene

<400> SEQUENCE: 6 gaaagggggt                                                                9

<210> SEQ ID NO 7
<211> LENGTH: 3654
<212> TYPE: DNA
<213> ORGANISM: Artificial Sequence
<220> FEATURE:
<223> OTHER INFORMATION: Description of Artificial Sequence:fragment
      used to clone Bacillus spaericus (Bs) binary toxin into plasmid
<221> NAME/KEY: CDS
<222> LOCATION: (741)..(2087)
<223> OTHER INFORMATION: 51.4 kD protein of Bs binary toxin
<221> NAME/KEY: CDS
<222> LOCATION: (2259)..(3371)
<223> OTHER INFORMATION: 41.9 kD protein of Bs binary toxin
```

```
<400> SEQUENCE: 7
gaattctatt ttcgatttca aattttccaa acttaaatat gattgaatgc ctgagaaagg      60
taatagagat gttttagttt attatgaagt attagggggcg tcttttaaat tcaatctatc    120
aatttgtgaa atatattact caaaacccaa taccattcta aaacttattc aaaatatata    180
ttgctttaaa agagcataca tactaaaaaa acaggcatct ttcgaactat agcgcataga    240
atactacggt gaatcaaaaa caaataaaat ttaggaggta tattcaagta tacaaaaaaa    300
ctttagtgtg aggggattta gataaaaagt attcgttatc cttataaatt aattcttaaa    360
catgcaccaa tgtatacatt aaataatatt atgtgaatta agtctatcaa tttaatttat    420
tatgttactt tatatttgat taataattgc aagtttaaaa tcataattta atgttgaaag    480
gccactattc taattaactt aaggagttgt ttatttgagc tcggtacccg gggataatct    540
tgaaaggagg gatgcctaaa aacgaagaac attaaaaaca tatatttgca ccgtctaatg    600
gatttatgaa aaatcatttt atcagtttga aaattatgta ttatgataag aaagtctaga    660
acgttattta atgaactttt taggttttaa ataatataat gagaagtatt ttttatcaat    720
gataaggaga tgaagaaagc atg tgc gat tca aaa gac aat tct ggc gtt tca    773
                        Met Cys Asp Ser Lys Asp Asn Ser Gly Val Ser
                          1               5                  10 gaa aaa tgc gga aag aaa ttt act aat tac ccg cta aat act act cct        821
Glu Lys Cys Gly Lys Lys Phe Thr Asn Tyr Pro Leu Asn Thr Thr Pro
            15                  20                  25 aca agc cta aat tat aac ctt cca gaa ata tca aaa aaa ttt tat aac        869
Thr Ser Leu Asn Tyr Asn Leu Pro Glu Ile Ser Lys Lys Phe Tyr Asn
                30                  35                  40 ctt aag aat aaa tat tca cgg aat ggt tat ggt tta tca aaa acc gaa        917
Leu Lys Asn Lys Tyr Ser Arg Asn Gly Tyr Gly Leu Ser Lys Thr Glu
     45                  50                  55 ttt cct tca agt atc gaa aat tgc cca tct aac gaa tat tca ata atg        965
Phe Pro Ser Ser Ile Glu Asn Cys Pro Ser Asn Glu Tyr Ser Ile Met
 60                  65                  70                  75 tat gat aat aaa gat cct cga ttc ttg att cgg ttt tta tta gat gat       1013
Tyr Asp Asn Lys Asp Pro Arg Phe Leu Ile Arg Phe Leu Leu Asp Asp
                80                  85                  90 ggt aga tat att att gca gat aga gac gat gga gaa gtt ttt gat gaa       1061
Gly Arg Tyr Ile Ile Ala Asp Arg Asp Asp Gly Glu Val Phe Asp Glu
         95                 100                 105 gca cct act tat ttg gat aat aac aat cac cct atc ata agt aga cat       1109
Ala Pro Thr Tyr Leu Asp Asn Asn Asn His Pro Ile Ile Ser Arg His
    110                 115                 120 tat acc gga gaa gag aga caa aag ttt gag cag gta ggt agt gga gat       1157
Tyr Thr Gly Glu Glu Arg Gln Lys Phe Glu Gln Val Gly Ser Gly Asp
125                 130                 135 tat att acg gga gag caa ttt ttt caa ttc tat aca caa aac aaa aca       1205
Tyr Ile Thr Gly Glu Gln Phe Phe Gln Phe Tyr Thr Gln Asn Lys Thr
140                 145                 150                 155 cgt gta ttg tca aat tgt agg gcg ctt gac agt agg aca ata tta cta       1253
Arg Val Leu Ser Asn Cys Arg Ala Leu Asp Ser Arg Thr Ile Leu Leu
             160                 165                 170 tct act gca aaa atc ttc cca att tac cct cca gct tct gaa act caa       1301
Ser Thr Ala Lys Ile Phe Pro Ile Tyr Pro Pro Ala Ser Glu Thr Gln
        175                 180                 185 cta aca gct ttc gtt aat agt tca ttt tat gct gcg gca att cct caa       1349
Leu Thr Ala Phe Val Asn Ser Ser Phe Tyr Ala Ala Ala Ile Pro Gln
    190                 195                 200 tta ccc caa aca tcc tta ctt gag aat att cct gag cct act agt ctc       1397
```

```
                                                              -continued
Leu Pro Gln Thr Ser Leu Leu Glu Asn Ile Pro Glu Pro Thr Ser Leu
    205                 210                 215 gat gat tct gga gta tta cca aaa gat gca gta aga gca gtt aaa gga        1445
Asp Asp Ser Gly Val Leu Pro Lys Asp Ala Val Arg Ala Val Lys Gly
220                 225                 230                 235 agt gcg cta tta cct tgt ata ata gta cat gat cct aat tta aac aat        1493
Ser Ala Leu Leu Pro Cys Ile Ile Val His Asp Pro Asn Leu Asn Asn
                240                 245                 250 tcc gat aaa atg aaa ttt aat acc tac tat ctt tta gaa tat aaa gaa        1541
Ser Asp Lys Met Lys Phe Asn Thr Tyr Tyr Leu Leu Glu Tyr Lys Glu
            255                 260                 265 tac tgg cat caa tta tgg tca caa att ata cct gct cat caa act gta        1589
Tyr Trp His Gln Leu Trp Ser Gln Ile Ile Pro Ala His Gln Thr Val
        270                 275                 280 aaa ata cag gaa cga aca gga ata tct gaa gtt gta caa aat agc atg        1637
Lys Ile Gln Glu Arg Thr Gly Ile Ser Glu Val Val Gln Asn Ser Met
    285                 290                 295 att gaa gat tta aat atg tat att gga gca gat ttt ggc atg ctt ttt        1685
Ile Glu Asp Leu Asn Met Tyr Ile Gly Ala Asp Phe Gly Met Leu Phe
300                 305                 310                 315 tat ttt aga tct agt gga ttt aag gaa caa ata aca agg ggg cta aat        1733
Tyr Phe Arg Ser Ser Gly Phe Lys Glu Gln Ile Thr Arg Gly Leu Asn
                320                 325                 330 agg cct tta tcc caa acg acc act cag tta gga gaa aga gta gaa gaa        1781
Arg Pro Leu Ser Gln Thr Thr Thr Gln Leu Gly Glu Arg Val Glu Glu
            335                 340                 345 atg gag tat tat aat tct aat gat ttg gat gtt aga tat gtg aaa tac        1829
Met Glu Tyr Tyr Asn Ser Asn Asp Leu Asp Val Arg Tyr Val Lys Tyr
        350                 355                 360 gca ttg gct aga gaa ttc aca cta aaa cgc gtt aat ggt gaa att gta        1877
Ala Leu Ala Arg Glu Phe Thr Leu Lys Arg Val Asn Gly Glu Ile Val
    365                 370                 375 aaa aat tgg gtt gct gta gat tat cga ttg gca ggt ata caa tcg tat        1925
Lys Asn Trp Val Ala Val Asp Tyr Arg Leu Ala Gly Ile Gln Ser Tyr
380                 385                 390                 395 cct aat gca cct ata act aat cca ctt acg cta aca aaa cat aca att        1973
Pro Asn Ala Pro Ile Thr Asn Pro Leu Thr Leu Thr Lys His Thr Ile
                400                 405                 410 att cga tgt gaa aat agt tac gat gga cac ata ttt aaa aca cct tta        2021
Ile Arg Cys Glu Asn Ser Tyr Asp Gly His Ile Phe Lys Thr Pro Leu
            415                 420                 425 atc ttt aaa aat ggt gaa gtt att gta aaa acg aat gaa gaa tta ata        2069
Ile Phe Lys Asn Gly Glu Val Ile Val Lys Thr Asn Glu Glu Leu Ile
        430                 435                 440 cct aaa att aac cag tga tactttaact tcaaatattc attaccatgt              2117
Pro Lys Ile Asn Gln
    445 tatttaaaat agtagataga tgaaataaat agtatatatt aagacaacaa cttaattttg      2177 acacataaga ataatttta aatgtataaa tagtatttag agtgttattg caatatattt       2237 tttgaaaggg agctaaaaga c atg aga aat ttg gat ttt att gat tct ttt        2288
              Met Arg Asn Leu Asp Phe Ile Asp Ser Phe
              450                 455 ata ccc aca gaa gga aag tac att cgc gtt atg gat ttt tat aat agc        2336
Ile Pro Thr Glu Gly Lys Tyr Ile Arg Val Met Asp Phe Tyr Asn Ser
460                 465                 470                 475 gag tat cct ttc tgt ata cat gca ccc tca gcc cct aat ggg gat atc        2384
Glu Tyr Pro Phe Cys Ile His Ala Pro Ser Ala Pro Asn Gly Asp Ile
                480                 485                 490
```

-continued

| | |
|---|---|
| atg aca gaa atc tgt agc aga gaa aat aat caa tat ttt att ttt ttt<br>Met Thr Glu Ile Cys Ser Arg Glu Asn Asn Gln Tyr Phe Ile Phe Phe<br>          495                  500               505 | 2432 |
| cct act gat gat ggt cga gta att att gca aat agg cat aat ggg tcc<br>Pro Thr Asp Asp Gly Arg Val Ile Ile Ala Asn Arg His Asn Gly Ser<br>          510                  515               520 | 2480 |
| gtt ttt acc gga gaa gcc aca agt gta gta tca gat atc tat act ggt<br>Val Phe Thr Gly Glu Ala Thr Ser Val Val Ser Asp Ile Tyr Thr Gly<br>     525                 530               535 | 2528 |
| agc cca tta cag ttt ttt aga gag gtc aaa aga act atg gca act tat<br>Ser Pro Leu Gln Phe Phe Arg Glu Val Lys Arg Thr Met Ala Thr Tyr<br>540               545                  550               555 | 2576 |
| tat tta gcg ata caa aat cct gaa tcc gca aca gat gtg aga gct cta<br>Tyr Leu Ala Ile Gln Asn Pro Glu Ser Ala Thr Asp Val Arg Ala Leu<br>               560                  565               570 | 2624 |
| gaa ccg cat tcc cat gag ctg cca tct cgc ctt tat tac act aac aat<br>Glu Pro His Ser His Glu Leu Pro Ser Arg Leu Tyr Tyr Thr Asn Asn<br>          575                  580               585 | 2672 |
| att gaa aat aat agc aac ata tta att tct aat aag gaa caa ata tat<br>Ile Glu Asn Asn Ser Asn Ile Leu Ile Ser Asn Lys Glu Gln Ile Tyr<br>          590                  595               600 | 2720 |
| tta acc ttg cct tca ctt cca gaa aac gag caa tac cct aaa act cca<br>Leu Thr Leu Pro Ser Leu Pro Glu Asn Glu Gln Tyr Pro Lys Thr Pro<br>605               610                  615 | 2768 |
| gta tta agc ggt atc gat gat ata gga cct aat caa tca gag aaa tca<br>Val Leu Ser Gly Ile Asp Asp Ile Gly Pro Asn Gln Ser Glu Lys Ser<br>620               625                  630               635 | 2816 |
| ata ata gga agt act ctt atc cca tgt ata atg gtt tcg gat ttt att<br>Ile Ile Gly Ser Thr Leu Ile Pro Cys Ile Met Val Ser Asp Phe Ile<br>               640                  645               650 | 2864 |
| agt ttg ggg gag aga atg aaa acc act cca tat tat tat gta aag cac<br>Ser Leu Gly Glu Arg Met Lys Thr Thr Pro Tyr Tyr Tyr Val Lys His<br>          655                  660               665 | 2912 |
| act caa tat tgg caa agc atg tgg tcc gcg ctc ttt cca ccc ggc tct<br>Thr Gln Tyr Trp Gln Ser Met Trp Ser Ala Leu Phe Pro Pro Gly Ser<br>               670                  675               680 | 2960 |
| aaa gag aca aaa act gag aaa tca ggt atc act gac act tct caa ata<br>Lys Glu Thr Lys Thr Glu Lys Ser Gly Ile Thr Asp Thr Ser Gln Ile<br>685               690                  695 | 3008 |
| agt atg act gac ggg att aat gtt tca atc gga gca gat ttc gga tta<br>Ser Met Thr Asp Gly Ile Asn Val Ser Ile Gly Ala Asp Phe Gly Leu<br>700               705                  710               715 | 3056 |
| agg ttt gga aat aaa acg ttt gga att aag ggg ggg ttc acc tat gat<br>Arg Phe Gly Asn Lys Thr Phe Gly Ile Lys Gly Gly Phe Thr Tyr Asp<br>               720                  725               730 | 3104 |
| aca aag act caa ata act aat acc tcc caa ttg tta ata gaa aca act<br>Thr Lys Thr Gln Ile Thr Asn Thr Ser Gln Leu Leu Ile Glu Thr Thr<br>          735                  740               745 | 3152 |
| tat act aga gaa tac aca aat aca gaa aat ttt cct gtt aga tat aca<br>Tyr Thr Arg Glu Tyr Thr Asn Thr Glu Asn Phe Pro Val Arg Tyr Thr<br>               750                  755               760 | 3200 |
| ggc tat gtt tta gcg tca gaa ttt act tta cat cgt agt gat gga act<br>Gly Tyr Val Leu Ala Ser Glu Phe Thr Leu His Arg Ser Asp Gly Thr<br>     765                 770               775 | 3248 |
| cag gtt aat acg atc cca tgg gtt gct tta aac gat aac tat aca aca<br>Gln Val Asn Thr Ile Pro Trp Val Ala Leu Asn Asp Asn Tyr Thr Thr<br>780               785                  790               795 | 3296 |
| ata gca aga tat cca cat ttt gca agt gaa cct tta cta gga aat aca<br>Ile Ala Arg Tyr Pro His Phe Ala Ser Glu Pro Leu Leu Gly Asn Thr<br>               800                  805               810 | 3344 |

-continued

```
aag att att aca gat gat caa aac taa atttaaacaa tattcttgaa              3391
Lys Ile Ile Thr Asp Asp Gln Asn
            815                 820 ctaatagatg ttaaatagaa caattaataa caatttaagt acttttggat tatagtgaag      3451
ggacctataa gcatagcttt taggtccctt ttaagttgct tttttcgtt tttagaatag       3511 tatagatagg ctacactaca ctaagttgga cagataaaat aagggttgt aaacttagac       3571 tattaaaaaa gggagagtgc tactatgaca cgtcaacatc gaacttttac actcgaatgt     3631
aaactgttgt tgtttggctg cag                                              3654

<210> SEQ ID NO 8
<211> LENGTH: 448
<212> TYPE: PRT
<213> ORGANISM: Artificial Sequence
<220> FEATURE:
<223> OTHER INFORMATION: Description of Artificial Sequence:51.4 kD
      protein

<400> SEQUENCE: 8

Met Cys Asp Ser Lys Asp Asn Ser Gly Val Ser Glu Lys Cys Gly Lys
  1               5                  10                  15

Lys Phe Thr Asn Tyr Pro Leu Asn Thr Thr Pro Thr Ser Leu Asn Tyr
                 20                  25                  30

Asn Leu Pro Glu Ile Ser Lys Lys Phe Tyr Asn Leu Lys Asn Lys Tyr
             35                  40                  45

Ser Arg Asn Gly Tyr Gly Leu Ser Lys Thr Glu Phe Pro Ser Ser Ile
         50                  55                  60

Glu Asn Cys Pro Ser Asn Glu Tyr Ser Ile Met Tyr Asp Asn Lys Asp
 65                  70                  75                  80

Pro Arg Phe Leu Ile Arg Phe Leu Leu Asp Asp Gly Arg Tyr Ile Ile
                 85                  90                  95

Ala Asp Arg Asp Asp Gly Glu Val Phe Asp Glu Ala Pro Thr Tyr Leu
            100                 105                 110

Asp Asn Asn Asn His Pro Ile Ile Ser Arg His Tyr Thr Gly Glu Glu
        115                 120                 125

Arg Gln Lys Phe Glu Gln Val Gly Ser Gly Asp Tyr Ile Thr Gly Glu
    130                 135                 140

Gln Phe Phe Gln Phe Tyr Thr Gln Asn Lys Thr Arg Val Leu Ser Asn
145                 150                 155                 160

Cys Arg Ala Leu Asp Ser Arg Thr Ile Leu Leu Ser Thr Ala Lys Ile
                165                 170                 175

Phe Pro Ile Tyr Pro Pro Ala Ser Glu Thr Gln Leu Thr Ala Phe Val
            180                 185                 190

Asn Ser Ser Phe Tyr Ala Ala Ala Ile Pro Gln Leu Pro Gln Thr Ser
        195                 200                 205

Leu Leu Glu Asn Ile Pro Glu Pro Thr Ser Leu Asp Asp Ser Gly Val
    210                 215                 220

Leu Pro Lys Asp Ala Val Arg Ala Val Lys Gly Ser Ala Leu Leu Pro
225                 230                 235                 240

Cys Ile Ile Val His Asp Pro Asn Leu Asn Asn Ser Asp Lys Met Lys
                245                 250                 255

Phe Asn Thr Tyr Tyr Leu Leu Glu Tyr Lys Glu Tyr Trp His Gln Leu
            260                 265                 270

Trp Ser Gln Ile Ile Pro Ala His Gln Thr Val Lys Ile Gln Glu Arg
        275                 280                 285
```

Thr Gly Ile Ser Glu Val Val Gln Asn Ser Met Ile Glu Asp Leu Asn
    290                 295                 300

Met Tyr Ile Gly Ala Asp Phe Gly Met Leu Phe Tyr Phe Arg Ser Ser
305                 310                 315                 320

Gly Phe Lys Glu Gln Ile Thr Arg Gly Leu Asn Arg Pro Leu Ser Gln
                325                 330                 335

Thr Thr Thr Gln Leu Gly Glu Arg Val Glu Met Glu Tyr Tyr Asn
            340                 345                 350

Ser Asn Asp Leu Asp Val Arg Tyr Val Lys Tyr Ala Leu Ala Arg Glu
        355                 360                 365

Phe Thr Leu Lys Arg Val Asn Gly Glu Ile Val Lys Asn Trp Val Ala
370                 375                 380

Val Asp Tyr Arg Leu Ala Gly Ile Gln Ser Tyr Pro Asn Ala Pro Ile
385                 390                 395                 400

Thr Asn Pro Leu Thr Leu Thr Lys His Thr Ile Ile Arg Cys Glu Asn
                405                 410                 415

Ser Tyr Asp Gly His Ile Phe Lys Thr Pro Leu Ile Phe Lys Asn Gly
            420                 425                 430

Glu Val Ile Val Lys Thr Asn Glu Glu Leu Ile Pro Lys Ile Asn Gln
        435                 440                 445

<210> SEQ ID NO 9
<211> LENGTH: 370
<212> TYPE: PRT
<213> ORGANISM: Artificial Sequence
<220> FEATURE:
<223> OTHER INFORMATION: Description of Artificial Sequence:41.9 kD
      protein

<400> SEQUENCE: 9

Met Arg Asn Leu Asp Phe Ile Asp Ser Phe Ile Pro Thr Glu Gly Lys
1               5                   10                  15

Tyr Ile Arg Val Met Asp Phe Tyr Asn Ser Glu Tyr Pro Phe Cys Ile
            20                  25                  30

His Ala Pro Ser Ala Pro Asn Gly Asp Ile Met Thr Glu Ile Cys Ser
        35                  40                  45

Arg Glu Asn Asn Gln Tyr Phe Ile Phe Pro Thr Asp Asp Gly Arg
    50                  55                  60

Val Ile Ile Ala Asn Arg His Asn Gly Ser Val Phe Thr Gly Glu Ala
65                  70                  75                  80

Thr Ser Val Val Ser Asp Ile Tyr Thr Gly Ser Pro Leu Gln Phe Phe
                85                  90                  95

Arg Glu Val Lys Arg Thr Met Ala Thr Tyr Tyr Leu Ala Ile Gln Asn
            100                 105                 110

Pro Glu Ser Ala Thr Asp Val Arg Ala Leu Glu Pro His Ser His Glu
        115                 120                 125

Leu Pro Ser Arg Leu Tyr Tyr Thr Asn Asn Ile Glu Asn Asn Ser Asn
130                 135                 140

Ile Leu Ile Ser Asn Lys Glu Gln Ile Tyr Leu Thr Leu Pro Ser Leu
145                 150                 155                 160

Pro Glu Asn Glu Gln Tyr Pro Lys Thr Pro Val Leu Ser Gly Ile Asp
                165                 170                 175

Asp Ile Gly Pro Asn Gln Ser Glu Lys Ser Ile Gly Ser Thr Leu
            180                 185                 190

Ile Pro Cys Ile Met Val Ser Asp Phe Ile Ser Leu Gly Glu Arg Met

-continued

```
                        195                 200                 205
Lys Thr Thr Pro Tyr Tyr Val Lys His Thr Gln Tyr Trp Gln Ser
    210                 215                 220

Met Trp Ser Ala Leu Phe Pro Pro Gly Ser Lys Glu Thr Lys Thr Glu
225                 230                 235                 240

Lys Ser Gly Ile Thr Asp Thr Ser Gln Ile Ser Met Thr Asp Gly Ile
                245                 250                 255

Asn Val Ser Ile Gly Ala Asp Phe Gly Leu Arg Phe Gly Asn Lys Thr
                260                 265                 270

Phe Gly Ile Lys Gly Gly Phe Thr Tyr Asp Thr Lys Thr Gln Ile Thr
            275                 280                 285

Asn Thr Ser Gln Leu Leu Ile Glu Thr Thr Tyr Thr Arg Glu Tyr Thr
    290                 295                 300

Asn Thr Glu Asn Phe Pro Val Arg Tyr Thr Gly Tyr Val Leu Ala Ser
305                 310                 315                 320

Glu Phe Thr Leu His Arg Ser Asp Gly Thr Gln Val Asn Thr Ile Pro
                325                 330                 335

Trp Val Ala Leu Asn Asp Asn Tyr Thr Thr Ile Ala Arg Tyr Pro His
                340                 345                 350

Phe Ala Ser Glu Pro Leu Leu Gly Asn Thr Lys Ile Ile Thr Asp Asp
            355                 360                 365

Gln Asn
    370

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence:PCR primer
      BSP-1

<400> SEQUENCE: 10
aactgcagct tgtcaacatg tgaagattaa aggtaacttt cag                    43

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:PCR primer
      BSP-2

<400> SEQUENCE: 11
aactgcagcc aaacaacaac agtttacatt cgagtgtaaa agttc                  45
```

What is claimed is:

1. A nucleic acid sequence comprising, in the following order,
   - a *B. thuringiensis* cry promoter selected from the group consisting of a BtI promoter, a BtII promoter, and a combination of a BtI and a BtII promoter,
   - a bacteria STAB-SI sequence,
   - a ribosome binding site, and
   - a sequence encoding one or both proteins of a *B. sphaericus* binary toxin.

2. The nucleic acid of claim 1, wherein the *B. thuringiensis* promoter is a cry1 promoter.

3. The nucleic acid of claim 1, wherein the *B. thuringiensis* promoter is selected from the group consisting of cry1Aa1, cry1Aa2, cry1Aa3, cry1Aa4, cry1Aa5, cry1Aa6, cry1Ba1, cry1Ba2, cry1Ca1, cry1Ca2, cry1Ca3, cry1Ca4, cry1Ca5, cry1Ca6, cry1Ca7, cry1Fa1 cry1Fa2.

4. The nucleic acid of claim 1 having a BtI promoter and a BtII promoter, wherein the BtI promoter and the BtII promoter are overlapping.

5. An expression vector comprising a nucleic acid of claim 1.

6. An expression vector comprising a nucleic acid of claim 2.

7. An expression vector comprising a nucleic acid of claim 3.

8. An expression vector comprising a nucleic acid of claim 4.

9. A host cell comprising an expression vector of claim 5.

10. A host cell comprising an expression vector of claim 6.

11. A host cell comprising an expression vector of claim 7.

12. A host cell comprising an expression vector of claim 8.

13. A host cell of claim 9 further comprising a cry11A 20 kD protein.

14. A host cell of claim 10, wherein the cell is a *B. thuringiensis* cell.

15. A host cell of claim 11, wherein the cell is a *B. thuringiensis* cell.

16. A host cell of claim 12, wherein the cell is a *B. thuringiensis* cell.

17. A host cell of claim 13, wherein the cell is a *B. thuringiensis* cell.

18. A nucleic acid sequence comprising, in the following order, a *B. thuringiensis* promoter which binds a sigma factor A protein, a bacterial STAB-SD sequence, a ribosome binding site, and a sequence encoding one or both proteins of a *B. sphaericus* binary toxin.

19. A method of enhancing production of *B. sphaericus* binary toxin in a host bacterial cell, said method comprising:
    a. transforming the host cell with a nucleic acid sequence comprising, in the following order, a *B. thuringiensis* promoter selected from the group consisting of a BtI promoter, a BtII promoter, and a combination of a Bt and a BtII promoter, a bacterial STAB-SD sequence, a ribosome binding site, and a sequence encoding one or both proteins of a *B. sphaericus* binary toxin; and
    b. expressing said nucleic acid sequence in the host cell;
whereby expression of said nucleic acid sequence enhances production of *B. sphaericus* binary toxin as compared to production of *B. sphaericus* binary toxin in a wild-type *B. sphaericus* cell that is not transformed with said nucleic acid sequence, and wherein said cell further expresses a 20 kD product of a cry11A gene.

20. The method of claim 19, wherein said host cell is a *B. thuringiensis* cell.

21. A method of increasing toxicity of a *B. thuringiensis* a bacterium to a mosquito, said method comprising the steps of:
    (a) transforming said bacterium with a nucleic acid sequence comprising, in the following order,
        a *B. thuringiensis* promoter selected from the group consisting of a BtI promoter, a BtII promoter, and a combination of a BtI and a BtII promoter,
        a bacterial STAB-SD sequence,
        a ribosome binding site, and
        a sequence encoding one or both proteins a *B. sphaericus* binary toxin;
    and,
    (b) expressing said nucleic acid sequence in the bacterium;
whereby expression of said nucleic acid sequence enhances production of *B. sphaericus* binary toxin as compared to production of *B. sphaericus* binary toxin in a wild-type *B. sphaericus* cell that is not transformed with said nucleic acid sequence, and wherein said bacterium further comprises a 20 kD product of the cry11A gene.

22. A recombinant cell of *B. sphaericus*, said cell comprising a nucleic acid sequence comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin.

23. The recombinant cell of claim 22, wherein the *B. thuringiensis* promoter is a cry promoter.

24. The recombinant cell of claim 22, wherein the *B. thuringiensis* promoter is selected from the group consisting of cry1Aa1, cry1Aa2, cry1Aa3, cry1Aa4, cry1Aa5, cry1Aa6, cry1Ba1, cry1Ba2, cry1Ca1, cry1Ca2, cry1Ca3, cry1Ca4, cry1Ca5, cry1Ca6, cry1Ca7, cry1Fa1, cry1Fa2, cyt1Aa1, cyt1Aa2, cyt1Aa3, and cyt1Aa4.

25. The recombinant cell of claim 24, wherein the *B. thuringiensis* promoter is a cyt1Aa1 promoter.

26. The recombinant cell of claim 22, wherein said cell further expresses a 20 kD product of a cry11A operon.

27. A method for increasing toxicity of a *B. sphaericus* cell to an insect, said method comprising
    (a) transforming the cell with a nucleic acid sequence comprising, in the following order, a *B. thuringiensis* promoter selected from the group consisting of a BtI promoter, a BtII promoter, and a combination of a BtI and a BtII promoter, a bacterial STAB-SD sequence, a ribosome binding site, and a sequence encoding one or both proteins of a *B. sphaericus* binary toxin; and
    (b) expressing said nucleic acid sequence in the host cell; whereby expression of said nucleic acid sequence enhances production of *B. sphaericus* binary toxin as compared to production of *B. sphaericus* binary toxin in a wild-type *B. sphaericus* cell that is not transformed with said nucleic acid sequence.

28. The method of claim 27, wherein *B. thuringiensis* promoter is a cry promoter.

29. The method of claim 27, wherein the *B. thuringiensis* promoter is a selected from the group consisting of cry1Aa1, cry1Aa2, cry1Aa3, cry1Aa4, cry1Aa5, cry1Aa6, cry1Ba1, cry1Ba2, cry1Ca1, cry1Ca2, cry1Ca3, cry1Ca4, cry1Ca5, cry1Ca6, cry1Ca7, cry1Fa1, cry1Fa2, cyt1Aa1, cyt1Aa2, cyt1Aa3, and cyt1Aa4.

30. The method of claim 29, wherein the *B. thuringiensis* promoter is a cyt1Aa1 promoter.

31. A method for suppressing resistance to a *B. sphaericus* binary toxin, said method comprising expressing a Bti Cyt1Aa1 protein in a *B. sphaericus* cell expressing said binary toxin.

32. A method for suppressing resistance to a *B. sphaericus* binary toxin, said method comprising administering Bti Cyt1Aa1 protein with said binary toxin.

33. A method of claim 32, wherein said Bti Cyt1Aa1 protein is in a powder of lysed, lyophilized Bti cells.

34. A method of claim 32, wherein said Bti Cyt1Aa1 protein is a purified protein.

35. A method of claim 32, wherein said Bti Cyt1Aa1 protein is administered in a Cyt1Aa1 protein to Bs ratio, selected from about 1:2 to about 1:50.

36. A method of claim 35, wherein said Bti Cyt1Aa1 protein is administered in a Cyt1Aa1 protein to Bs ratio of about 1:10.

37. A method of enhancing production of *B. sphaericus* binary toxin in a host *B. sphaericus* cell, said method comprising:
    a. transforming the host cell with a nucleic acid sequence comprising, in the following order,
        (i) a *B. thuringiensis* promoter selected from the group consisting of a BtI promoter, a BtII promoter, and a combination of a BtI and a BtII promoter,
        (ii) a bacterial STAB-SD sequence,
        (iii) a ribosome binding site, and
        (iv) a sequence encoding one or both proteins of a *B. sphaericus* binary toxin; and
    b. expressing said nucleic acid sequence in the host cell; whereby expression of said nucleic acid sequence enhances production of *B. sphaericus* binary toxin as compared to production of *B. sphaericus* binary toxin in a wild-type *B. sphaericus* cell that is not transformed with said nucleic acid sequence.

* * * * *